United States Patent [19]
Metzker et al.

[11] Patent Number: 5,861,287
[45] Date of Patent: Jan. 19, 1999

[54] ALTERNATIVE DYE-LABELED PRIMERS FOR AUTOMATED DNA SEQUENCING

[75] Inventors: Michael L. Metzker; Richard A. Gibbs, both of Houston, Tex.

[73] Assignee: Baylor College of Medicine, Houston, Tex.

[21] Appl. No.: 540,228

[22] Filed: Oct. 6, 1995

Related U.S. Application Data

[63] Continuation-in-part of Ser. No. 494,216, Jun. 23, 1995, Pat. No. 5,614,386.
[51] Int. Cl.$^6$ .............................. C12P 19/34; C12Q 1/68; C07H 21/04; C07H 21/02
[52] U.S. Cl. .................. 435/91.1; 435/6; 435/5; 435/91.2; 536/24.3; 536/24.32; 536/24.33; 536/23.1
[58] Field of Search .................. 435/6, 5, 91.1, 435/91.2; 536/24.3–24.33

[56] References Cited

U.S. PATENT DOCUMENTS

| | | | |
|---|---|---|---|
| 4,318,846 | 3/1982 | Khanna | 260/112 B |
| 4,744,339 | 5/1988 | Haugland et al. | 548/405 |
| 4,755,458 | 7/1988 | Rabbani | 536/27 |
| 4,774,339 | 9/1988 | Haughland et al. | 548/405 |
| 4,811,218 | 3/1989 | Hunkapiller et al. | 364/413.01 |
| 4,855,225 | 8/1989 | Fung et al. | 435/6 |
| 5,151,507 | 9/1992 | Hobbs | 536/23 |
| 5,171,534 | 12/1992 | Smith et al. | 422/82.05 |
| 5,188,934 | 2/1993 | Menchen et al. | 435/6 |
| 5,241,060 | 8/1993 | Englehardt | 435/5 |
| 5,366,603 | 11/1994 | Middendorf et al. | 204/182.8 |
| 5,366,860 | 11/1994 | Bergot et al. | 435/6 |
| 5,370,777 | 12/1994 | Guttman et al. | 204/182.8 |

FOREIGN PATENT DOCUMENTS 9521266  8/1995  WIPO .

OTHER PUBLICATIONS

Metzker et al., Termination of DNA synthesis by novel 3'–modified–deoxyribonucleoside 5'–triphosphates, *Nucleic Acids Research*, 22:4259–4267 (1994).
Drmanac, et al., Sequencing of Megabase Plus DNA by Hybridization: Theory of the Method: *Genomics*, 4:114–28 (1989).
Khrapko et al., An oligonucleotide hybridization approach to DNA sequencing, *FEB*, 256:118–22 (1989).
Strezoska et al., DNA sequencing by hybridization: 100 bases read by a non–gel–based method; *PNAS*, 88:10089–93 (1991).
Boude et al., Enhanced DNA sequencing by hybridization; *PNAS*, 91:3072–76 (1994).
Pease et al., Light–generated oligonucleotide arrays for rapid DNA sequence analysis; *PNAS*, 91:5022–26 (1994).
Studier, A strategy for high–volume sequencing of cosmid DNAs: Random and directed priming with a library of oligonucleotides; *PNAS*, 86:6917–21 (1989).
Kieleczawa et al., DNA Sequencing by Primer Walking with Strings of Contiguous Hexamers; *Science*, 258:1787–91 (1992).
Swerdlow et al., Capillary gel electrophoresis for rapid, high resolution DNA sequencing; *Nucleic Acids Research*, 18:1415–19 (1990).
Karger et al., Multiwavelength fluorescence detection for DNA sequencing using capillary electrophoresis, *Nucleic Acids Research*, 19:4955–62 (1991).
Ruiz–Martinez et al., DNA Sequencing by Capillary Electrophoresis with Replaceable Linear Polyacrylamide and Laser–Inducted Fluorescence Detection; *Anal Chem.*, 65:2851–58.
Prober et al., A System for Rapid DNA Sequencing with Fluorescent Chain–Terminating Dideoxynucleotides, *Science*, 238:336–41 (1987).
Smith et al., Fluorescence detection in automated DNA sequence analysis; *Nature*, 321:674–79 (1986).
Lee et al., NAR 20: 247124–83, 1992.
Haugland, Report from Energy Research Abstracts 17(6) Abstr. No. 16972, 1990.

*Primary Examiner*—W. Gary Jones
*Assistant Examiner*—Dianne Rees
*Attorney, Agent, or Firm*—Fulbright & Jaworski LLP

[57] ABSTRACT

Methods for the use of a class of dyes for improved DNA sequencing are provided. A new class of dyes, BODIPY® fluorophores, has been described recently. The parent heterocyclic molecule of the BODIPY® fluorophores is a dipyrromethenboron difluoride compound which is modified to create a broad class of spectrally-discriminating fluorophores. The present invention provides methods for the use of BODIPY® fluorophore-labeled DNA for dye-primer sequencing in which the BODIPY®s are attached to the 5' end of sequencing primers. BODIPY® fluorophores have improved spectral characteristics compared to conventional fluorescein and rhodamine dyes. BODIPY® fluorophores have narrower band width, insensitivity to solvent or pH, and improved photostability, thus, BODIPY® fluorophores lead to improved DNA sequencing and/or detection in any method where electrophoresis and detection of DNA is required. Additionally, the spectral properties of the BODIPY® fluorophores are sufficiently similar in wavelength and intensity to be used with conventional equipment known in the art.

19 Claims, 12 Drawing Sheets

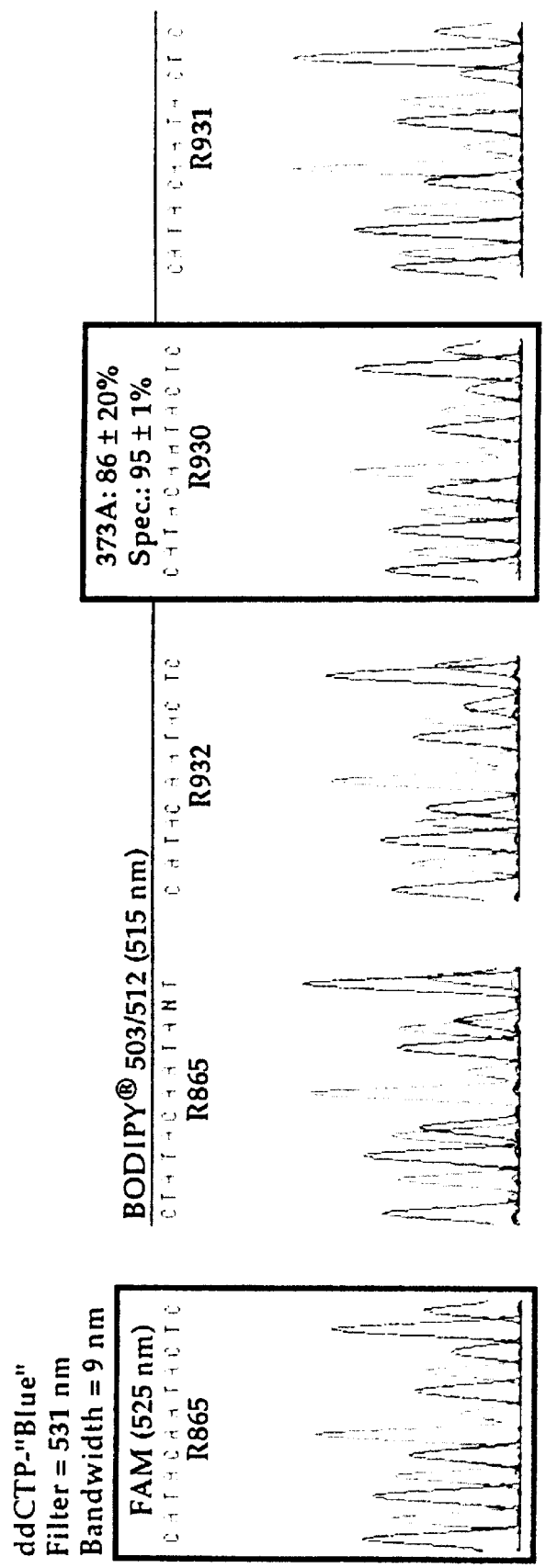

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "oligonucleotide"

( i i i ) HYPOTHETICAL: YES ( i v ) ANTI-SENSE: NO ( v i i i ) POSITION IN GENOME:
( C ) UNITS: 18 bp ( x i ) SEQUENCE DESCRIPTION: SEQ ID NO:1:

TGTAAAACGA CGGCCAGT    18

( 2 ) INFORMATION FOR SEQ ID NO:2:

( i ) SEQUENCE CHARACTERISTICS:

( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "oligonucleotide"

( i i i ) HYPOTHETICAL: YES ( i v ) ANTI-SENSE: NO ( v i i i ) POSITION IN GENOME:
    ( C ) UNITS: 21 bp ( x i ) SEQUENCE DESCRIPTION: SEQ ID NO:2:

CGTTGTAAAA CGACGGCCAG T                            2 1

( 2 ) INFORMATION FOR SEQ ID NO:3:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "oligonucleotide"

( i i i ) HYPOTHETICAL: YES ( i v ) ANTI-SENSE: NO ( v i i i ) POSITION IN GENOME:
    ( C ) UNITS: 19 bp ( x i ) SEQUENCE DESCRIPTION: SEQ ID NO:3:

TTGTAAAACG ACGGCCAGT                               1 9

ALTERNATIVE DYE-LABELED PRIMERS FOR AUTOMATED DNA SEQUENCING

This application is a continuation-in-part of U.S. Ser. No. 08/494,216 filed Jun. 23, 1995 now U.S. Pat. No. 5,614,386.

This invention was supported in part by a grant from the United States Government through the National Institutes of Health (Grant Nos. P30HG00210 (NIH) and T32HG00003 (NIH-NCHGR). The U.S. Government has certain rights in this invention.

FIELD OF THE INVENTION

This invention relates generally to methods for the use of a class of dyes for improved DNA sequencing and labelling of DNA fragments for genetic analysis.

BACKGROUND

The present invention relates to methods for the use of a new class of dyes for DNA sequencing and labelling of DNA fragments for genetic analysis. The ability to determine the sequence of DNA is critical for understanding the function and control of genes and for applying many of the basic techniques of molecular biology. Native DNA consists of two linear polymers, or strands, of nucleotides. Each strand is a chain of nucleosides linked by phosphodiester bonds. The two strands are held together in an antiparallel orientation by hydrogen bonds between complementary bases of the nucleotides of the two strands: deoxyadenosine (A) pairs with thymidine (T) and deoxyguanosine (G) pairs with deoxycytidine (C).

The development of reliable methods for sequence analysis of DNA (deoxyribonucleic acid) and RNA (ribonucleic acid) has been essential to the success of recombinant DNA and genetic engineering. When used with the other techniques of modern molecular biology, nucleic acid sequencing allows dissection of animal, plant and viral genomes into discrete genes with defined chemical structure. Since the function of a biological molecule is determined by its structure, defining the structure of a gene is crucial to the eventual useful manipulation of this basic unit of hereditary information. Once genes can be isolated and characterized, they can be modified to produce desired changes in their structure that allow the production of gene products—proteins—with different properties than those possessed by the original gene products.

The development of modern nucleic acid sequencing methods involved parallel developments in a variety of techniques. One was the emergence of simple and reliable methods for cloning small to medium-sized strands of DNA into bacterial plasmids, bacteriophages, and small animal viruses. Cloning allowed the production of pure DNA in sufficient quantities to allow chemical analysis. Another was the use of gel electrophoretic methods for high resolution separation of oligonucleotides on the basis of size. The key development, however, was the introduction of methods of generating sets of fragments of cloned, purified DNA that contain, in their collection of lengths, the information necessary to define the sequence of the nucleotides comprising the parent DNA molecules.

Presently there are several approaches to DNA sequence determination, see, e.g., the dideoxy chain termination method, Sanger et al., *Proc. Natl. Acad. Sci.*, 74:5463–67 (1977); the chemical degradation method, Maxam et al., *Proc. Natl. Acad. Sci.*, 74:560–564 (1977); and hybridization methods, Drmanac et al., *Genomics*, 4:114–28 (1989), Khrapko, *FEB* 256:118–22 (1989). The chain termination method has been improved in several ways, and serves as the basis for all currently available automated DNA sequencing machines. See, e.g., Sanger et al., *J. Mol. Biol.*, 143:161–78 (1980); Schreier et al., *J. Mol. Biol.*, 129:169–72 (1979); Smith et al., *Nucleic Acids Research*, 13:2399–2412 (1985); Smith et al., *Nature*, 321:674–79 (1987) and U.S. Pat. No. 5,171,534; Prober et al., *Science*, 238:336–41 (1987); Section II, *Meth. Enzymol.*, 155:51–334 (1987); Church et al., *Science*, 240:185–88 (1988); Swerdlow and Gesteland, *Nucleic Acids Research*, 18: 1415–19 (1989); Ruiz-Martinez et al., *Anal. Chem.*, 2851–58 (1993); Studier, *PNAS*, 86:6917–21 (1989); Kieleczawa et al., *Science*, 258:1787–91; and Connell et al., *Biotechniques*, 5:342–348 (1987).

The method developed by Sanger is referred to as the dideoxy chain termination method. In a commonly-used variation of this method, a DNA segment is cloned into a single-stranded DNA phage such as M13. These phage DNAs can serve as templates for the primed synthesis of the complementary strand by conventional DNA polymerases. The primer is either a synthetic oligonucleotide or a restriction fragment isolated from the parental recombinant DNA that hybridizes specifically to a region of the M13 vector near the 3' end of the cloned insert. In each of four sequencing reactions, the primed synthesis is carried out in the presence of enough of the dideoxy analog of one of the four possible deoxynucleotides so that the growing chains are randomly terminated by the incorporation of these "deadend" nucleotides. The relative concentration of dideoxy to deoxy forms is adjusted to give a spread of termination events corresponding to all the possible chain lengths that can be resolved by gel electrophoresis. The products from each of the four primed synthesis reactions are loaded into individual lanes and are separated by polyacrylamide gel electrophoresis. Radioactive label incorporated in the growing chains are used to develop an autoradiogram image of the pattern of the DNA in each electrophoresis lane. The sequence of the deoxynucleotides in the cloned DNA is determined from an examination of the pattern of bands in the four lanes. Because the products from each of the four synthesis reactions must be run on separate gel lanes, there are problems with comparing band mobilities in the different lanes.

Turning to automated DNA sequencing machines, in general, fragments having different terminating bases can be labeled with different fluorescent dyes, which are attached either to a primer for dye-primer sequencing in which the fluorescent dyes are attached to the 5' end of the primers, e.g., Smith et al. (1987, cited above), or to the base of dideoxynucleotides for dye terminator sequencing in which the fluorescent dyes are attached to the $C^7$ position of a purine terminating base and the $C^5$ of a pyrimidine terminating base, e.g., Prober et al. (cited above). A fluorescence detector then can be used to detect the fluorophore-labeled DNA fragments. The four different dideoxy-terminated samples can be run in four separate lanes or, if labeled differentially, in the same lane. The method of Fung, et al., U.S. Pat. No. 4,855,225, uses a set of four chromophores or fluorophores with different absorption or fluorescent maxima. Each of these tags is coupled chemically to the primer used to initiate the synthesis of the fragment strands. In turn, each tagged primer is then paired with one of the dideoxynucleotides and used in the primed synthesis reaction with conventional DNA polymerases. The labeled fragments are then combined and loaded onto the same gel column for electrophoretic separation. Base sequence is determined by analyzing the fluorescent signals emitted by the fragments as they pass a stationary detector during the separation process.

Obtaining a set of dyes to label the different fragments is a major difficulty in automated DNA sequencing systems. First, it is difficult to find three or more dyes that do not have emission bands which overlap significantly since the typical emission band halfwidth for organic fluorescent dyes is about 40–80 nanometers (nm) and the width of the visible spectrum is only about 350–400 nm. Second, even if dyes with non-overlapping emission bands are found, the set may still be unsuitable for DNA sequencing if the respective fluorescent efficiencies are too low. For example, Pringle et al., DNA Core Facilities Newsletter, 1:15–21 (1988), present data indicating that increased gel loading cannot compensate low fluorescent efficiencies.

Another difficulty with obtaining an appropriate set of dyes is that when several fluorescent dyes are used concurrently, excitation becomes difficult because the absorption bands of the dyes are often widely separated. The most efficient excitation occurs when each dye is illuminated at the wavelength corresponding to its absorption band maximum. Thus, one often is forced to compromise between the sensitivity of the detection system and the increased cost of providing separate excitation sources for each dye. In addition, when the number of differently sized fragments in a single column of a gel is greater than a few hundred, the physiochemical properties of the dyes and the means by which they are linked to the fragments become critical because the charge, molecular weight, and conformation of the dyes and linkers must not effect adversely the electrophoretic mobilities of closely-sized fragments. Changes in electrophoretic mobility can result in extensive band broadening or reversal of band positions on the gel, thereby destroying the correspondence between the order of bands and the order of the bases in the nucleic acid sequence. Due to the many problems associated with altered electrophoretic mobility, correction of mobility discrepancies by computer software is necessary in prior art systems. Finally, the fluorescent dyes must be compatible with the chemistry used to create or manipulate the fragments. For example, in the chain termination method the dyes used to label primers and/or the dideoxy chain terminators must not interfere with the activity of the polymerase or reverse transcriptase employed.

Because of these severe constraints, only a few sets of fluorescent dyes have been found that can be used in DNA sequencing, particularly automated DNA sequencing, and in other diagnostic and analytical techniques, e.g., Smith et al. (1985, cited above); Prober et al. (cited above); Hood et al., European patent application 8500960; Bergot et al. (cited above); Fung et al. (cited above); Connell et al. (cited above); Lee, et al., Nucleic Acids Research, 20:2471–83 (1992); and Menchen et al., U.S. Pat. No. 5,188,934.

In view of the above, DNA sequencing would be advanced significantly by the availability of new sets of fluorescent dyes which (1) are physiochemically similar, (2) permit detection of spatially overlapping target substances, such as closely spaced bands of DNA on a gel, (3) extend the number of bases that can be determined on a single gel column by current methods of automated DNA sequencing, (4) are amenable for use with a wide range of preparative and manipulative techniques, and (5) otherwise satisfy the numerous requirements listed above. See, Bergot, et al. (cited above).

Until the present invention, one problem encountered was that each fluorophore altered the "normal" electrophoretic mobility of the corresponding termination products during gel electrophoresis such that software correction files were needed to generate accurate, evenly-spaced DNA sequences. See, Smith et al., Nature, 321:674–79 (1986) and U.S. Pat. No. 5,171,534. Thus, the set of discriminating fluorophores described in the literature is small, and the search for improved, alternative dyes has been difficult at best.

There are several different chemical modifications that have been attempted to correct for differences in gel mobility between different dye-labeled primers in automated DNA sequencing. Generally, fluorescein and its derivative dyes labeled in DNA sequencing reactions have different gel mobilities in comparison to rhodamine and its derivative dyes labeled in DNA sequencing reactions. Fluorescein and its derivative dye-labeled reactions typically move through the gel faster (sometimes greater than one base position) than rhodamine and its derivative dye-labeled reactions. For example, if using the −21M13 universal sequencing primer, each fluorophore is coupled to the primer via different linker arm lengths. Both fluoresceins are coupled to the primer using a two-carbon amino linker arm while both rhodamines are coupled to the primer using six-carbon amino linker arm. Mobility correction software, however, is required additionally to generate properly spaced DNA termination fragments. Another example involves custom sequencing primers. These primers refer to any oligonucleotide sequence that can act as a suitable DNA sequencing primer. To all custom sequencing primers, a 5'-leader sequence (5'-CAGGA) must be coupled to the primer and custom sequencing primers must use the M13RP1 mobility correction software to generate properly-spaced DNA termination fragments. The leader sequence is the first five bases of the reverse M13RP1 sequencing primer. M13RP1 is the mobility software file used to generate properly spaced DNA termination fragments for the reverse sequencing primer.

A new class of dyes, 4,4-difluoro-4-bora-3A,4A-diaza-s-indacene (BODIPY®) fluorophores, has been recently described. See, Haugland, et al., Molecular Probes: Handbook of Fluorescent Probes and Research Chemicals, pp. 24–32, and U.S. Pat. No. 4,774,339. The parent heterocyclic molecule of the BODIPY® fluorophores is a dipyrrometheneboron difluoride compound and which is modified to create a broad class of spectrally-discriminating fluorophores, see FIG. 1. The conventional naming of these dyes is BODIPY® followed by their approximate absorption/emission maxima, e.g., BODIPY® 530/550.

In addition to the specifically-cited references above, additional prior art techniques include the following:

U.S. Pat. No. 4,318,846 to Khanna et al. is drawn to diether symmetrically-substituted fluoresceins having at least one anionic group and a linking functionality. Depending on the site of substitution, the compounds can be used as fluorescers absorbing at wavelengths in excess of 500 nm. The compounds can be used as labels in fluorescent immunoassays.

U.S. Pat. No. 4,811,218 to Hunkapiller et al. is drawn to a real-time, automated nucleic acid sequencing apparatus which permits more than one clone to be sequenced at the same time.

U.S. Pat. No. 4,855,225 to Fung et al., is drawn to a method for detecting up to four sets of oligonucleotides that have been differentially-labeled with fluorophores, two of the sets with substituted fluoresceins and two sets with substituted rhodamines, and separated by gel electrophoresis.

U.S. Pat. No. 5,366,860 to Bergot et al., is drawn to a method for detecting up to four sets of oligonucleotides that have been differentially-labeled with fluorophores, all rhodamines with different substitutions, and separated by gel electrophoresis.

U.S. Pat. No. 5,188,934 to Menchen, et al., is drawn to a method for detecting up to four sets of oligonucleotides that have been differentially-labeled with fluorophores, all fluoresceins with different substitutions, and separated by gel electrophoresis.

U.S. Pat. No. 5,171,534 to Smith et al. describes a system for the electrophoretic analysis of DNA fragments produced in DNA sequencing operations. The system comprises a source of chromophore or fluorescent tagged DNA fragments, a zone for contacting an electrophoresis gel, means for introducing said tagged DNA fragments to said zone and photometric means for monitoring the tagged DNA fragments as they move through the gel.

U.S. Pat. No. 5,366,603 is drawn to automatic DNA sequencing wherein the DNA is marked with near infrared fluorescent dyes.

U.S. Pat. No. 5,241,060 to Englehardt, et al., is drawn to labeled nucleotides and polynucleotides with the formula PM-SM-BASE-Sig, where PM is a phosphate moiety, SM is a sugar moiety, BASE is a purine, pyrimidine or 7-deazapurine moiety, and Sig is a detectable moiety that is covalently attached to the BASE entity at a position other than the $C^5$ position when BASE is a pyrimidine, at a position other than the $C^8$ position when BASE is a purine and at a position other than the $C^7$ position when BASE is a 7-deazapurine.

U.S. Pat. No. 4,755,458 to Rabbani, et al., is drawn to compositions for detecting the presence of a nucleotides sequence of interest. The composition includes a first polynucleotide molecule is substantially complementary to and capable of hybridizing with a specific sequence of interest and which is labeled with a first detectable marker; a second polynucleotide molecule is not substantially complementary to and is not capable of hybridizing with the specific sequence of interest and is labeled with the same, first detectable marker; and a third polynucleotide molecule that is substantially complementary to or substantially identical to the second polynucleotide but is unlabeled or labeled with a second detectable marker.

U.S. Pat. No. 5,151,507 to Hobbs, et al., drawn to alkynylamino-nucleotides useful as chain terminating substrates for DNA sequencing.

SUMMARY OF THE INVENTION 4,4-Difluoro-4-bora-3A,4A-diaza-s-indacene (BODIPY®) fluorophores have improved spectral characteristics compared to conventional fluorescein and rhodamine dyes. The BODIPY® fluorophores have narrower band width, insensitivity to solvent or pH, and improved photostability. Thus, the use of BODIPY® fluorophores lead to improved DNA sequencing or analysis of DNA fragments in any method where electrophoresis of BODIPY®-labeled DNA is required.

It is an object of the present invention to provide methods for the use of a class of dyes particularly suited for DNA sequencing.

It is a particular object of the present invention to provide methods for the use of BODIPY® fluorophores for any method of DNA sequencing in which polynucleotide products of the sequencing reaction are 5'-end-labelled with said BODIPY® fluorophores.

It is an additional particular object of the present invention to provide methods for the use of BODIPY® fluorophores in the chemical cleavage method of DNA sequencing.

It is a further object of the present invention to provide methods for the use of BODIPY® fluorophores which have been chemically-modified so that a BODIPY® fluorophore can be used to replace a prior art 5'-end-labelled fluorophore in DNA sequencing and conventional software may be used. BODIPY® fluorophores can be used in one out of the four reactions, two out of the four reactions or three out of the four reactions or in all four reactions.

If BODIPY® fluorophores are used in four out of the four reactions, a particular object of the present invention is to provide methods for the use of BODIPY® fluorophores for automated DNA sequencing which, since the particular BODIPY® fluorophores alter the mobility of the corresponding termination products in the same way, nullifies the need for software correction to generate evenly-spaced DNA sequences.

An additional object of the present invention is to provide methods for the use of BODIPY® fluorophores for DNA sequencing wherein the BODIPY® fluorophore is attached at the 5' end of the polynucleotide product of the sequencing reaction and at the 3' end or at one or more internal positions of the products of the sequencing reaction.

Thus, in accomplishing the foregoing objects, there is provided a method for analysis of DNA fragments wherein said DNA fragments are labelled with at least one BODIPY® fluorophore. Further, in accomplishing the foregoing objects, there is provided in accordance with the present invention, a method for distinguishing polynucleotides having different 3'-terminal dideoxynucleotides in any method of DNA sequencing requiring electrophoresis of the products of the sequencing reactions, the method comprising the steps of: forming a mixture of a first, a second, a third, and a fourth class of polynucleotides, each polynucleotide in the first class having a 3'-terminal dideoxyadenosine and being labeled with a first fluorophore; each polynucleotide in the second class having a 3'-terminal dideoxycytidine and being labeled with a second fluorophore; each polynucleotide in the third class having a 3'-terminal dideoxyguanosine and being labeled with a third fluorophore; and each polynucleotide in the fourth class having a 3'-terminal dideoxythymidine and being labeled with a fourth fluorophore; wherein at least one of said fluorophores is a BODIPY® fluorophore, and, wherein if said first, second, third and fourth fluorophores are all different, said polynucleotides can be electrophoresed in a same or different lanes; or wherein if any of said first, second, third or fourth fluorophores are the same, said polynucleotides labeled with said same fluorophores are electrophoresed in separate lanes; electrophoretically separating on a gel by size the polynucleotides; illuminating with an illumination beam the bands on the gel, the illumination beam being capable of causing the fluorophores to fluoresce; and identifying the classes of polynucleotides in the bands by the fluorescence or absorption spectrum of the fluorophores.

Other and further objects, features and advantages will be apparent and the invention more readily understood from a reading of the following specification and by reference to the accompanying drawings forming a part thereof, wherein the examples of the presently preferred embodiments of the invention are given for the purposes of disclosure.

DESCRIPTION OF THE DRAWINGS

The file of this patent contains at least one drawing executed in color. Copies of this patent with the color drawing(s) will be provided by the Patent and Trademark Office upon request and payment of the necessary fee.

FIGS. 3A through 3E: Depicts the results of a dye-labeled substitution experiment. DNA sequencing reactions were generated by solid-phase Bst sequencing. The region shown corresponds to approximately 230 to 240 bases (Blue), 160 to 170 bases (Green), 290 to 300 bases (Black), and 200 to 210 bases (Red) in the sequencing read. 373A raw files were analyzed by the ABI sequencing analysis version 2.1.0 software program using the ABI50 (standard) base caller with the M13RP1 mobility correction file. The 1 max (parentheses) for dye-primers was determined using a Model F-4010 fluorescence spectrophotometer (Hitachi, Ltd) in 1× TBE buffer (0.089M Tris-borate, 0.002M $NA_2EDTA$) containing 7M urea. Signal strength was measured using a 373A sequencer (373A) or using a fluorescence spectrophotometer (Spec.). 373A measurements were determined by M13 cycling sequencing reactions of four different molecular clones. The relative intensity values were determined by normalizing the BODIPY® dye signal to the remaining dye signals and comparing it to its normalized conventional dye signal. Spec. measurements were performed in duplicate and determined by comparing the fluorescence intensity at 1 max of BODIPY® dye-primers to conventional dye-primers. FAM and BODIPY® 503/512 were excited at 488 nm and all remaining dyes were at 514 nm.

Figure 1:
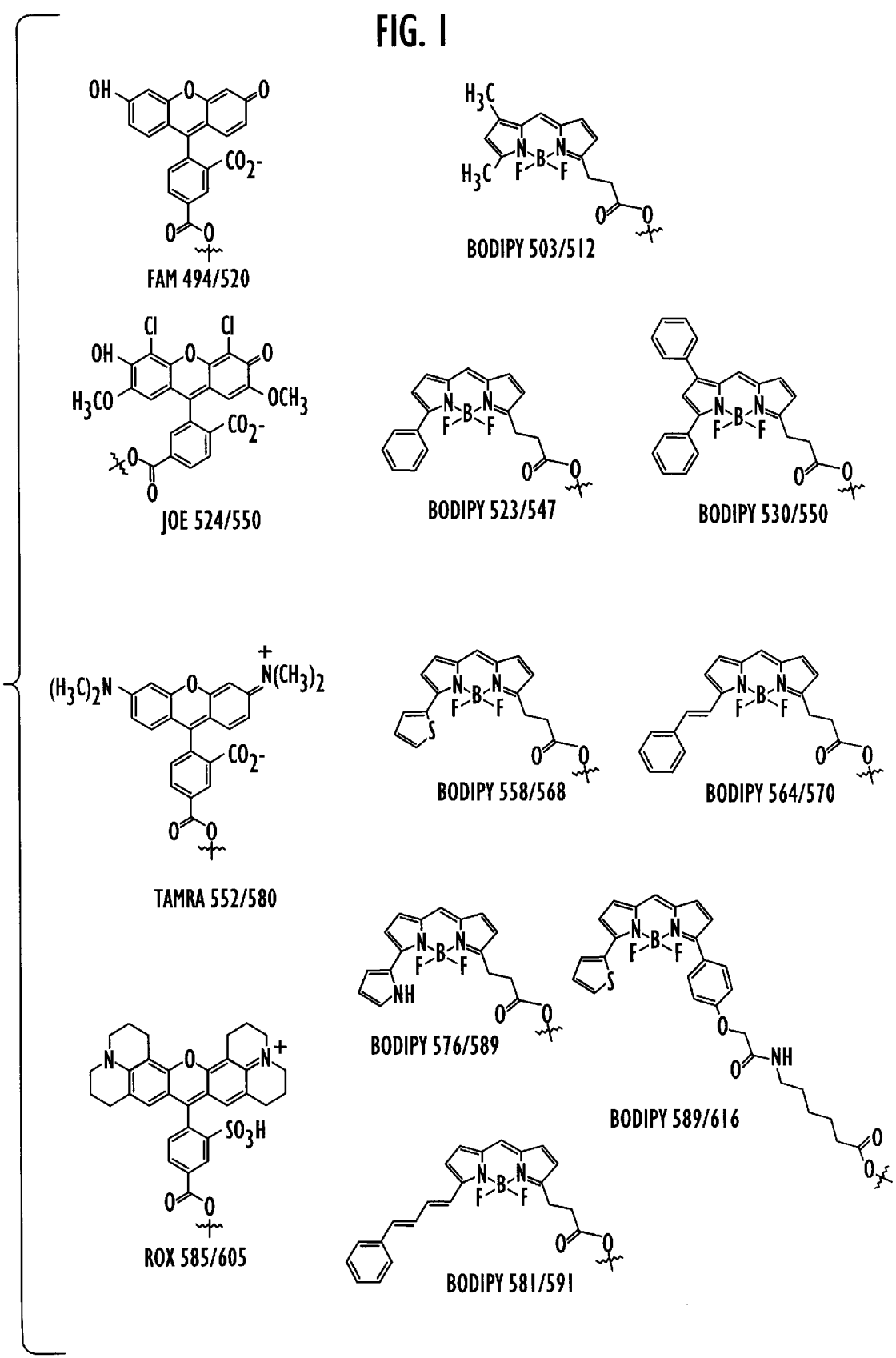
FIG. 1: Chemical structures of several DNA sequencing fluorophores are shown.

The drawings and figures are not to scale and certain features mentioned may be exaggerated in scale or shown in schematic form in the interest of clarity and conciseness.

DETAILED DESCRIPTION OF THE INVENTION

It will be apparent to one skilled in the art that various substitutions and modifications may be made to the invention disclosed herein without departing from the scope and the spirit of the invention.

As used herein, "BODIPY®" shall refer to a broad class of modified, spectrally-discriminating fluorophores wherein the parent heterocyclic molecule is a dipyrromethenboron difluoride compound, specifically, a 4,4-difluoro-4-bora-3A, 4A-diaza-s-indacene compound. Specific BODIPY® fluorophores useful in the present invention include BODIPY®s with adsorption maxima of about 450 to 700, and emission maxima of about 450 to 700. Preferred embodiments include BODIPY®s with adsorption maxima of about 480 to 650, and emission maxima of about 480 to 650. Examples of preferred embodiment BODIPY®s include BODIPY® 503/512-SE (4,4-difluoro-5,7-dimethyl-4-bora-3a,4a-diaza-s-indacene-3-propionicacid), BODIPY®523/547 (4,4-difluoro-5-phenyl-4-bora-3a,4a-diaza-s-indacene-3-propionic acid), BODIPY® 530/550 (4,4-difluoro-5,7-diphenyl-4-bora-3a,4a-diaza-s-indacene-3-propionic acid), BODIPY® 558/568 (4,4-difluoro-5-(2-thienyl)-4-bora-3a,4a-diaza-s-indacene-3-propionic acid), BODIPY®564/570 (4,4-difluoro-5-styryl-4-bora-3a,4a-diaza-s-indacene-3-propionicacid), BODIPY®576/589(4,4-difluoro-5-(2-pyrrolyl)-4-bora-3a,4a-diaza-s-indacene-3-propionic acid), BODIPY® 581/591 (4,4-difluoro-5-(4-phenyl-1,3-butadienyl)-4-bora-3a,4a-diaza-s-indacene-3-propionic acid), and BODIPY® 589/616 (6-(((4-(4,4-difluoro-5-(2-thienyl)-4-bora-3a,4a-diaza-s-indacene-3-yl)phenoxy) acetyl)amino)hexanoic acid).

As used herein, "DNA sequencing" refers to the process of determining the nucleic acid sequence of a DNA strand of interest.

As used herein "automated DNA sequencing" refers to determining the sequence of a DNA strand of interest using an apparatus comprising an area having an electrophoresis gel, means for introducing labeled DNA fragments to the gel area, and photometric means for monitoring said labeled DNA fragments as they move through the gel. "Automated DNA sequencer" refers to the instrument which is able to perform automated DNA sequencing.

As used herein, "sequencing primer" means a synthetic oligonucleotide, restriction fragment, enzymatically-synthesized DNA fragment, or the like which hybridizes specifically to a region proximate to the region of DNA to be sequenced. "Universal sequencing primer" refers to commonly-used primers known in the art, generally one that hybridizes specifically to a region of the M13 vector near the 5' end of the cloned insert. Specific examples of universal sequencing primers known in the art are −21M13, M13-40 and −36M13.

As used herein, "5' position" refers to the 5' position on the deoxyribose moiety of a polynucleotide.

As used herein, "base attachment" or "dye-terminator" refers to a molecule, particularly a fluorescent dye, attached to the $C^7$ position of a purine terminating base or the $C^5$ of a pyrimidine terminating base.

As used herein, "3' position" refers to the 3' position on the deoxyribose moiety of a nucleotide.

As used herein, "FAM" shall refer to 5-carboxy-fluorescein, "JOE" shall refer to 2',7'-dimethoxy-4',5'-dichloro-6-carboxy-fluorescein, "TAMRA" shall refer to N,N,N',N'-tetramethyl-6-carboxy-rhodamine, "ROX" shall refer to 6-carboxy-X-rhodamine.

As used herein, electrophoresis "lanes" or "tracks" or "columns" refers to the particular path in the electrophoretic medium in which the sequencing products are run. For example, the sequencing products terminating in dideoxyadenosine, dideoxycytodine, dideoxyguanosine or dideoxythymidine may be run in four separate lanes, or, if labeled differentially, in the same lane.

As used herein, "linkers" or "linker arms" refers to molecules that tether a dye to a primer. Typical linker molecules include alkanes of various lengths.

One novel aspect of the present invention is to provide a method for distinguishing polynucleotides having different 3'-terminal dideoxynucleotides in any method of DNA sequencing requiring electrophoresis of the products of the sequencing reactions, the method comprising the steps of: forming a mixture of a first, a second, a third, and a fourth class of polynucleotides, each polynucleotide in the first class having a 3'-terminal dideoxyadenosine and being labeled at the 5' position with a first fluorophore; each polynucleotide in the second class having a 3'-terminal dideoxycytidine and being labeled at the 5' position with a second fluorophore; each polynucleotide in the third class having a 3'-terminal dideoxyguanosine and being labeled at the 5' position with a third fluorophore; and each polynucleotide in the fourth class having a 3'-terminal dideoxythymidine and being labeled at the 5' position with a fourth fluorophore; wherein at least one of said fluorophores is a BODIPY® fluorophore, and, wherein if said first, second, third and fourth fluorophores are all different, said polynucleotides can be electrophoresed in a same or a different lane; or wherein if any of said first, second, third or fourth fluorophores are the same, said polynucleotides labeled with said same fluorophores are electrophoresed in separate lanes; electrophoretically separating on a gel by size the polynucleotides; illuminating with an illumination beam the bands on the gel, the illumination beam being capable of causing the fluorophores to fluoresce; and identifying the classes of polynucleotides in the bands by the fluorescence or absorption spectrum of the fluorophores.

Another aspect of the present invention allows BODIPY® fluorophores to be used in combination with prior art fluorophores and commercially-available software. This method involves distinguishing polynucleotides having different 3'-terminal dideoxynucleotides in the chain termination method of DNA sequencing, the method comprising the steps of: forming a mixture of a first, a second, a third, and a fourth class of polynucleotides, each polynucleotide in the first class having a 3'-terminal dideoxyadenosine and being labeled at the 5' position with BODIPY® 523/547, BODIPY® 530/550 or JOE; each polynucleotide in the second class having a 3'-terminal dideoxycytidine and being labeled at the 5' position with BODIPY® 503/512 or FAM; each polynucleotide in the third class having a 3'-terminal dideoxyguanosine and being labeled at the 5' position with BODIPY® 558/568, BODIPY® 564/570 or TAMRA; and each polynucleotide in the fourth class having a 3'-terminal dideoxythymidine and being labeled at the 5' position with BODIPY® 581/591, BODIPY® 589/616 or ROX; wherein at least one of the classes is labeled with a BODIPY® fluorophore; electrophoretically separating on a gel by size the polynucleotides; illuminating with an illumination beam the bands on the gel, the illumination beam being capable of causing the fluorophores to fluoresce; and identifying the classes of polynucleotides in the bands by the fluorescence or absorption spectrum of the fluorophores.

In another aspect of the present invention, there is provided a method of distinguishing polynucleotides having different 3'-terminal dideoxynucleotides in the chain termination method of DNA sequencing, the method comprising the steps of: forming a mixture of a first, a second, a third, and a fourth class of polynucleotides, each polynucleotide in the first class having a 3'-terminal dideoxyadenosine and being labeled at the 5' position with a first BODIPY® fluorophore; each polynucleotide in the second class having a 3'-terminal dideoxycytidine and being labeled at the 5' position with a second BODIPY® fluorophore; each polynucleotide in the third class having a 3'-terminal dideoxyguanosine and being labeled at the 5' position with a third BODIPY® fluorophore; and each polynucleotide in the fourth class having a 3'-terminal dideoxythymidine and being labeled at the 5' position with a fourth BODIPY® fluorophore; wherein said first, second, third and fourth BODIPY® fluorophores are all different; electrophoretically separating on a gel by size the polynucleotides; illuminating with an illumination beam bands of said gel, said illumination beam being capable of causing said BODIPY® fluorophores to fluoresce; and identifying the classes of polynucleotides in the bands by the fluorescence or absorption spectrum of the dyes.

In a preferred embodiment, said BODIPY® fluorophores have an adsorption maxima of about 450 to 700, and an emission maxima of about 450 to 700. In a more preferred embodiment, said BODIPY® fluorophores have adsorption maxima of about 500 to 625, and an emission maxima of about 500 to 625.

In one aspect of the present invention, said 3'-terminal dideoxyadenosine is labeled at the 5' position with BODIPY® 523/547; said 3'-terminal dideoxycytidine is labeled at the 5' position with BODIPY® 503/512; said 3'-terminal dideoxyguanosine is labeled at the 5' position with BODIPY® 564/570; and said 3'-terminal dideoxythymidine is labeled at the 5' position with BODIPY® 581/591. Labeling the polynucleotides in this manner allows for the use of conventional, commercially-available software. However, it should be clear that one skilled in the art of computer software design that software could be altered such that the software could read different BODIPY® dyes attached to different classes of polynucleotides by way of different linker arm chemistries.

In a preferred embodiment, said chain termination method of DNA sequencing is performed by an automated DNA sequencing instrument.

In a preferred embodiment, the method of the present invention further includes the step of extending from a primer a plurality of polynucleotides by means of a DNA polymerase suitable for DNA sequencing or a reverse transcriptase suitable for DNA sequencing in the presence of dideoxyadenosine triphosphate, dideoxycytosine triphosphate, dideoxyguanosine triphosphate, and dideoxythymidine triphosphate to form said first, second, third, and fourth classes of polynucleotides.

In another preferred embodiment of the present invention, said DNA polymerase is selected from the group of ThermoSequenase, Klenow fragment, SEQUENASE®, Bst DNA polymerase, AMPLITAQ® DNA polymerase, Pfu (exo-)DNA polymerase, rTth DNA polymerase or VENT (EXO)® DNA polymerase, and said reverse transcriptase is selected from the group of AMV-RT or M-MuLV-RT.

In another embodiment of the present invention, said BODIPY® fluorophores are coupled to a primer suitable for sequencing by linkers. In a more preferred embodiment of this aspect of the present invention, said linker arms are selected from the group of $(CH_2)_3$, $(CH_2)_6$, and $(CH_2)_{12}$.

In yet another aspect of the present invention, said polynucleotide is labeled with more than one fluorophore, wherein said fluorophores include at least one BODIPY® fluorophore and at least one additional fluorophore. In a more preferred embodiment of this aspect of the invention, said additional fluorophore has an adsorption maxima of about 475 to about 650. In another embodiment of this aspect of the present invention, said additional fluorophore is a BODIPY® fluorophore or FAM.

In an additional aspect to the present invention, methods are provided for the use of BODIPY® fluorophores for DNA sequencing wherein the BODIPY® fluorophore is attached at the 5' end of the products of the sequencing reaction and at the 3' end of the product of the sequencing reaction or at one or more internal positions of the products of the sequencing reaction.

In an another aspect of the present invention there is provided a method for distinguishing polynucleotide sequences in a hybridization method of DNA sequencing, said method comprising the steps of: synthesizing a first, a second, a third and a fourth class of oligonucleotides, wherein all of said classes of oligonucleotides have a same length, said first, second, third and fourth classes of oligonucleotides differ from the oligonucleotides of each other class by one nucleotide base at a 3', a 5' or an internal position, and each oligonucleotide of the first class has a deoxyadenosine at said position and is labeled at the 5' position with a first fluorophore; each oligonucleotide in the second class has a deoxycytidine at said position and is labeled at the 5' position with a second fluorophore; each oligonucleotide in the third class having a deoxyguanosine at said position and is labeled at the 5' position with a third fluorophore; and each oligonucleotide in the fourth class has a deoxythymidine at said position and is labeled at the 5' position with a fourth fluorophore; wherein at least one of said fluorophores is a BODIPY® fluorophore; hybridizing said oligonucleotides to a single-stranded DNA target immobilized to a solid support, wherein said solid support is in a grid format, to form a hybridized product; washing said hybridized product to remove any unhybridized oligonucleotide or target; illuminating with an illumination beam the solid support, said illumination beam being capable of causing said BODIPY® fluorophores to fluoresce; and identifying the classes of polynucleotides in the bands by the fluorescence or absorption spectrum of the dyes.

In an important aspect of the present invention, there is provided a method for genetic analysis of DNA fragments wherein said DNA fragments are labelled with at least one BODIPY® fluorophore.

The following examples are offered by way of illustration and are not included to limit the invention in any manner. The examples show the procedures for synthesizing BODIPY®-tagged primers and performing DNA sequencing with said primers.

EXAMPLE 1

4,4-Difluoro-4-bora-3A,4A-diaza-s-indacene (BODIPY®) Fluorophores Can Substitute for Conventional Sequencing Dyes To examine the role of BODIPY® dyes in automated DNA sequencing, substitution experiments were performed by replacing a conventional dye with a corresponding BODIPY® dye having similar absorption/emission maxima. Different linker arms coupled to a universal sequencing primer were synthesized to chemically alter BODIPY® dye-labeled primers to mimic the gel mobility pattern of conventional dye-labeled primers. Thus, BODIPY® dyes can replace one or more prior art dyes. or Fluorophores.

A. Reagents

DNA synthesis reagents were purchased from Applied Biosystems, Inc. (ABI) except 5'-amino-modifier C3, C6, and C12 phosphoramidites were purchased from Glen Research. Oligonucleotides R865, R932, R930, and R931 (FIG. 2) were synthesized trityl-on (0.2 $\mu$mole scale) using either an ABI model 380B or model 394 DNA synthesizer and purified using Nensorb™ 20 columns according to the manufacturer's protocol (du Pont de Nemours & Co.). FAM-NHS, JOE-NHS, TAMRA-NHS, and ROX-NHS ester were purchased from ABI. 5-FAM-SE and BODIPY®-SE dyes were purchased from Molecular Probes and resuspended in anhydrous DMSO (50 mg/mL).

B. Preparation of fluorescent primers

Purified R865 primer (1.0 $\mu$mole) was resuspended in 240 $\mu$L of 0.5M NaHCO$_3$/Na$_2$CO$_3$ (pH 9.0) buffer and divided into eight aliquots. To each tube, 3 $\mu$L of either FAM-NHS ester, 5-FAM-SE, JOE-NHS ester, TAMRA-NHS ester, ROX-NHS ester, or 5 $\mu$L of BODIPY® 503/512-SE, BODIPY® 523/547-SE, BODIPY® 530/550-SE, BODIPY® 558/568-SE, BODIPY® 564/570-SE, BODIPY® 576/589-SE, BODIPY® 581/591-SE, or BODIPY® 589/616-SE, was added. Purified R930, R931, or R932 primers (0.6 $\mu$mole) were resuspended in 200 $\mu$L of 0.5M NaHCO$_3$/Na$_2$CO$_3$, pH 9.0 buffer and divided into seven aliquots. To each tube, 5 $\mu$L of either BODIPY® 503/512-SE, BODIPY® 530/550-SE, BODIPY® 558/568-SE, BODIPY® 564/570-SE, BODIPY® 576/589-SE, BODIPY® 581/591-SE, or BODIPY® 589/616-SE, respectively was added. Reactions were incubated at 25° C. for 16 h. Following ethanol precipitation, dye-labeled primers were purified by reverse-phase high performance liquid chromatography (RP-HPLC). Fluorescent primers were resuspended in 10 mM Tris-HCl, pH 8.0 and 1 mM EDTA and diluted to 0.4 pmol/$\mu$L.

C. RP-HPLC purification of oligonucleotides

The RP-HPLC hardware system used consists of a Beckman model 127 gradient solvent module, a Rheodyne model 7125 injector, an Applied Biosystems (ABI) model 759A absorbance detector, and a Spectra-Physics model SP4600 DataJet integrator. Gradient RP-HPLC was performed using an ABI aquapore RP-300 column (4.6 mm×250 mm) where "Buffer A" is 100 mM triethylammonium acetate (TEAA), pH 7.0, and "Buffer B" is 100 mM TEAA, 70% (v/v) acetonitrile. Dye-labeled oligonucleotides were purified using the following gradient conditions: 20% Buffer B, 5 min.; 20%–40% Buffer B, 30 min.; 40%–100% Buffer B, 18 min.; 100% Buffer B, 5 min. at a flow rate of 1.0 mL per min.

D. Results 4,4-Difluoro-4-bora-3A,4A-diaza-s-indacene (BODIPY®) fluorophores can substitute for conventional sequencing dyes or fluorophores. The chemical structures of different fluorophores and their corresponding absorption/emission maxima are shown in FIG. 1. FAM, JOE, TAMRA, and ROX are four conventional fluorophores utilized in automated DNA sequencing. To examine the role of BODIPY® fluorophores in DNA sequencing, substitution experiments were performed replacing conventional dye-labeled primers with BODIPY®s that correspond to the emission spectrum of the prior art, dye-labeled primers. Oligonucleotide R865, (FIG. 2), was dye-labeled with the fluorophores listed in FIG. 1 and purified by RP-HPLC. DNA sequencing reactions were generated by either solid-phase Bst sequencing or Taq cycle-sequencing. The results of the substitution experiment are shown in FIG. 3. Here, three dye-labeled termination products (i.e., FAM, TAMRA, and ROX) were generated, combined with either JOE or BODIPY® 530/550 termination products, and analyzed by automated DNA sequencing. With the exception of BODIPY® 589/616 reactions, BODIPY® 503/512-, BODIPY® 523/547-, BODIPY® 530/550-, BODIPY® 558/

568-, BODIPY® 564/570-, BODIPY® 576/589-, and BODIPY® 581/591-labeled termination products migrated approximately ¾ to 1 base pair faster through the gel than FAM-, JOE-, TAMRA-, or ROX-labeled termination products, respectively. The discrepancy between the two reactions is the result of the altered mobility of the different dye structures.

Figure 2A:
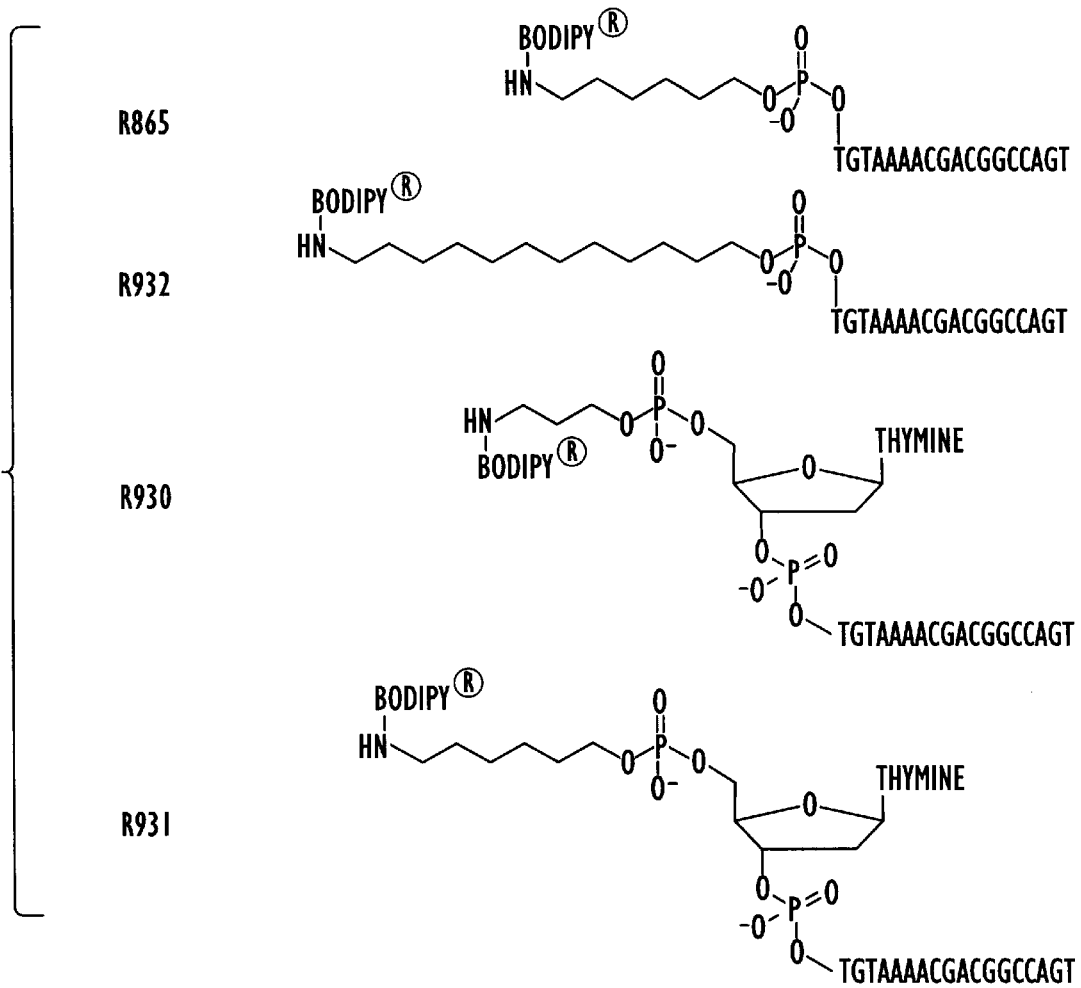
FIGS. 2A and 2B: 5'-end modifications of (2A) single dye-labeled primers: R865, R932, R930, and R931; and (2B) double dye-labeled primers FET-3 and BET-3 are shown. Since different protecting groups block the linker arm amines, BET primers were first labeled internally with BODIPY® 503/512. Following removal of the monomethoxytrityl group, BET primers were end-labeled with the BODIPY® dye set. The $(CH_2)_n$ for BET primers correspond to $(CH_2)_3$ for BODIPY® 581/591 and $(CH_2)_6$ for BODIPY® 503/512, BODIPY® 523/547, and BODIPY® 564/570 dyes. Primers R865, R932, R930, R931 and BET-3 show modifications to SEQ ID No. 1; and primer FET-3 shows a modification to SEQ. ID No. 2.
Figure 2B:
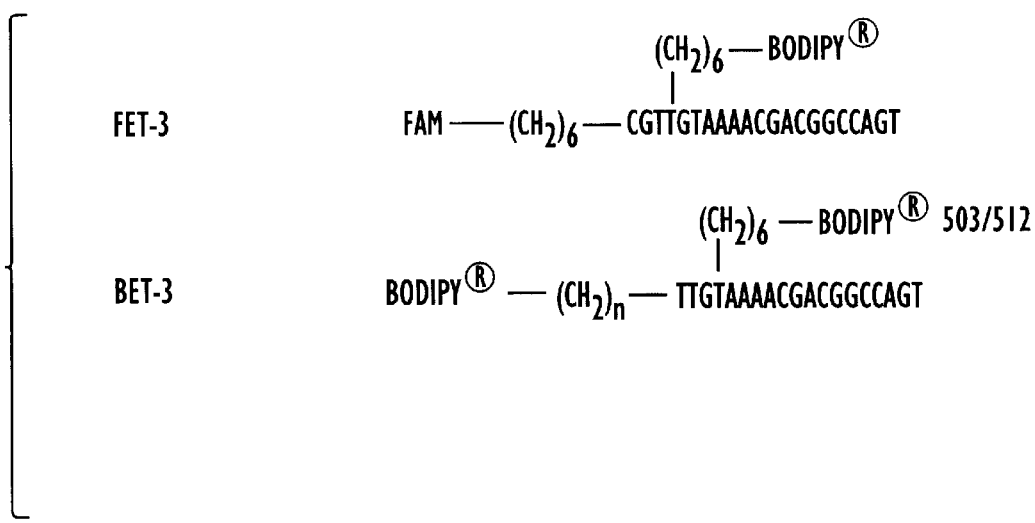
Figure 3B:
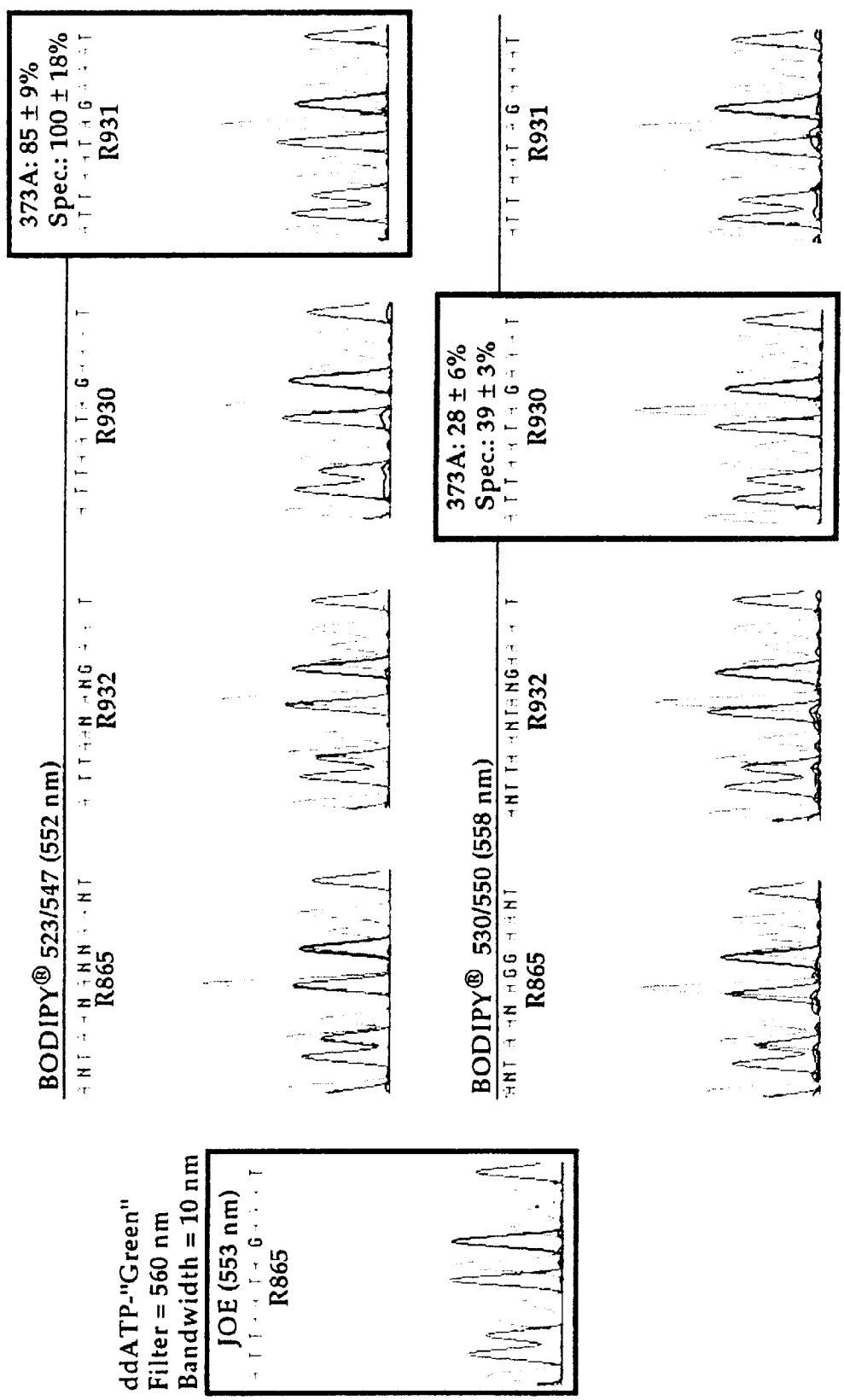
Figure 3C:
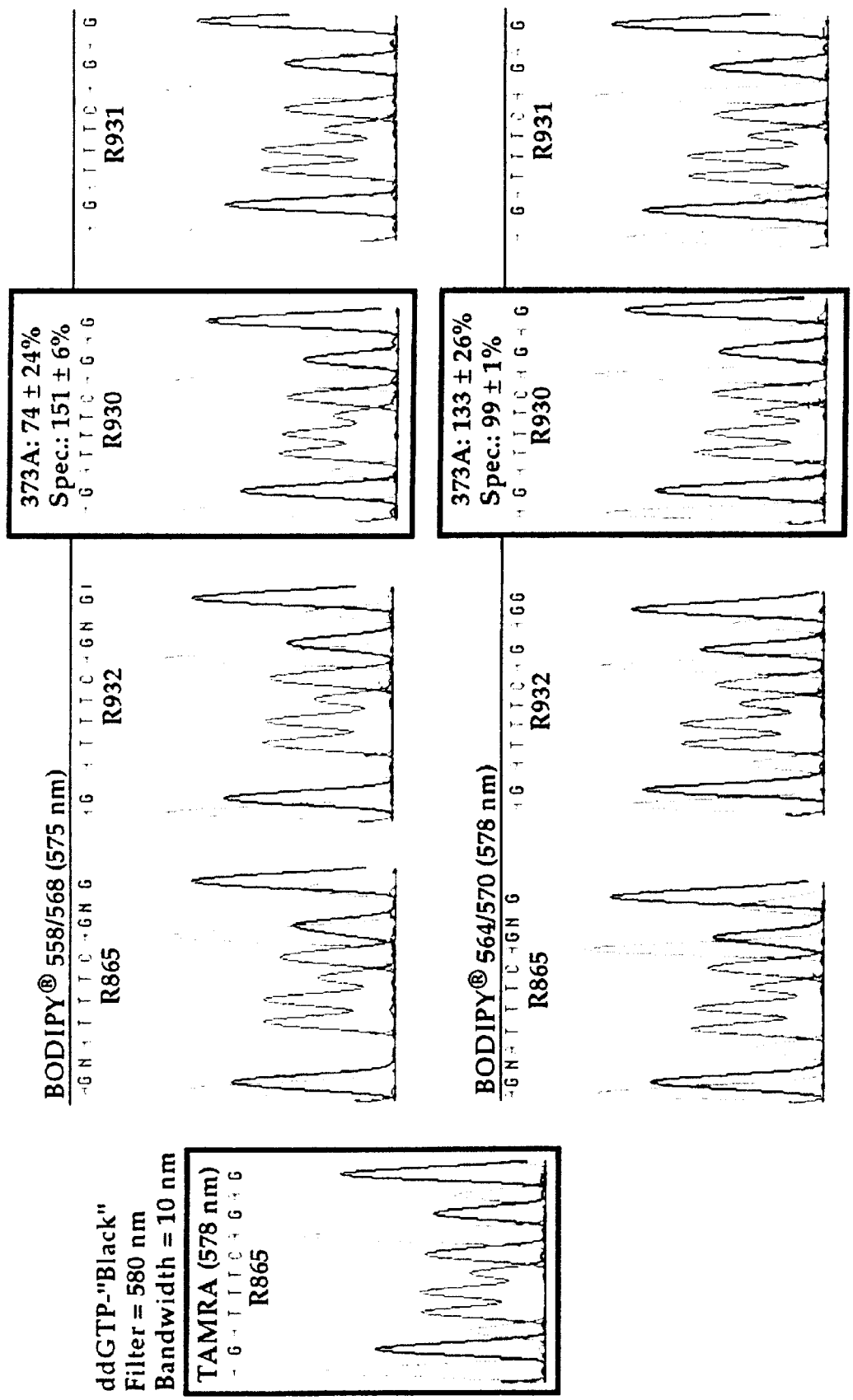
Figure 3D:
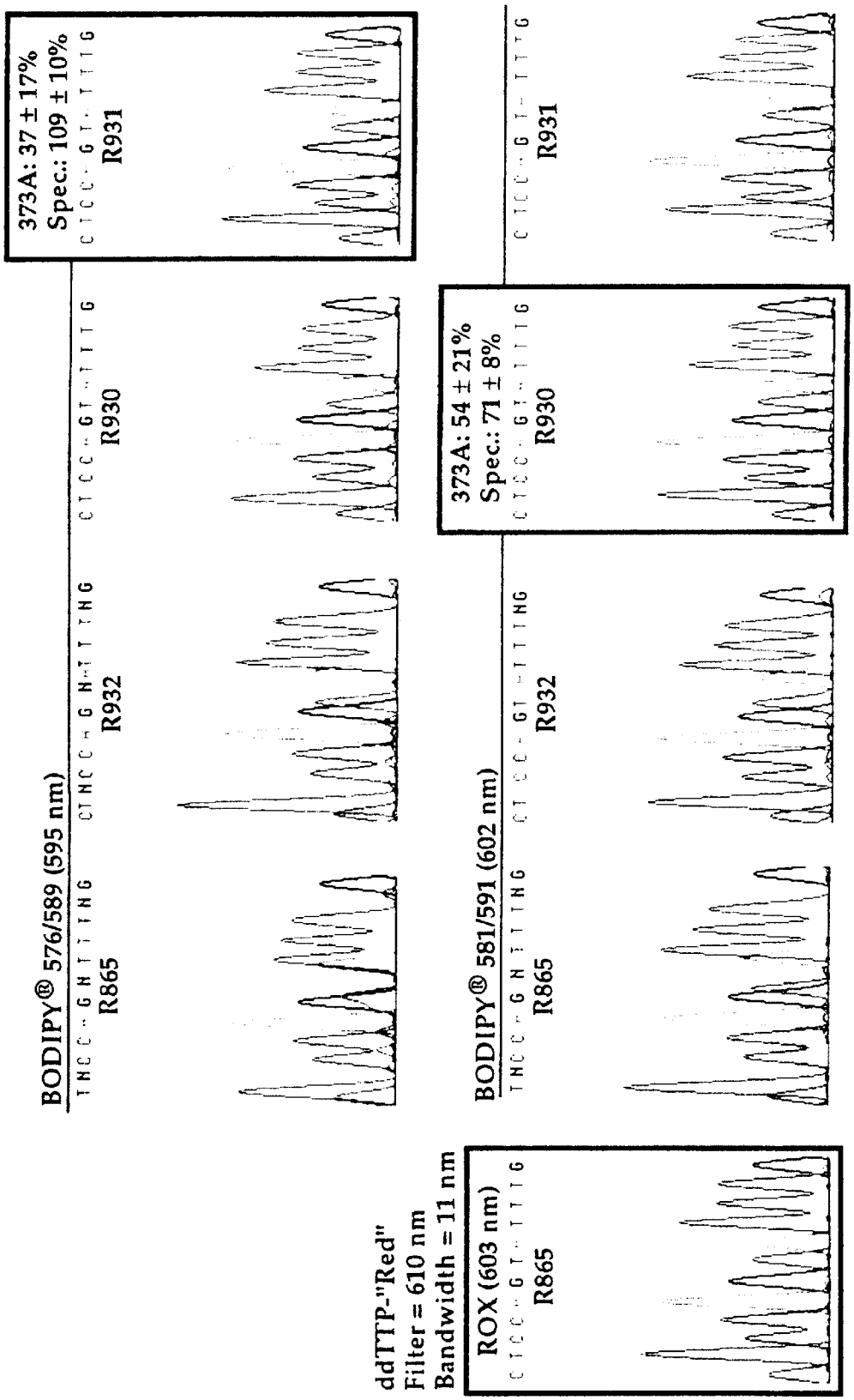
Figure 3E:
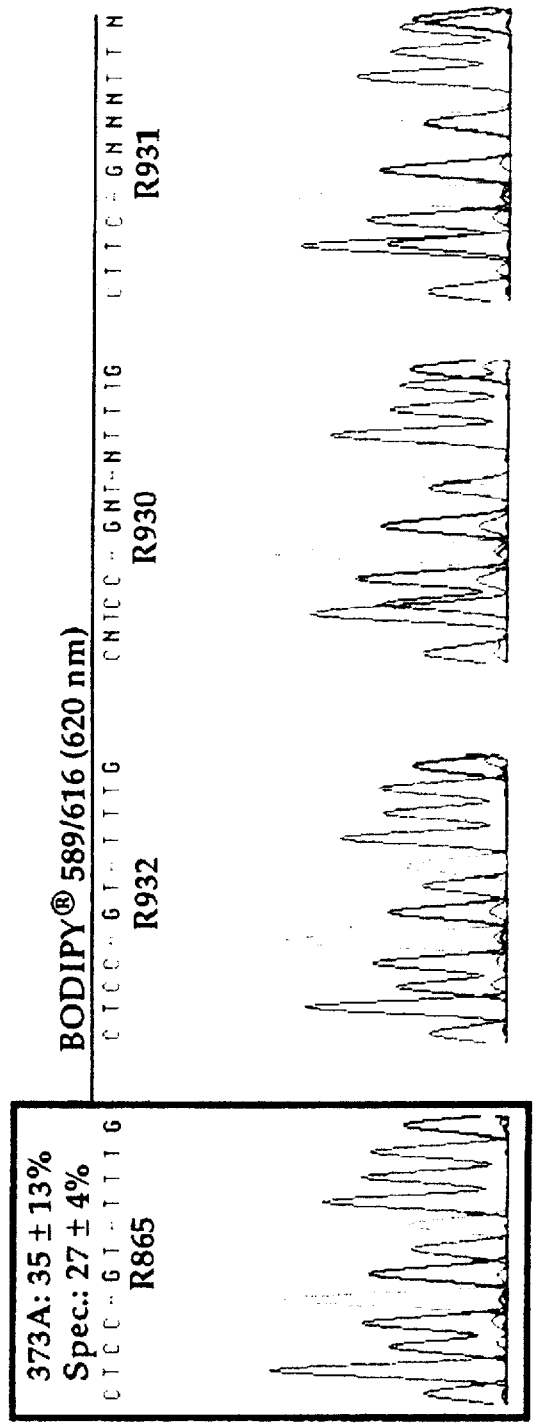

Although software modifications could have been employed to correct dye-primer mobility shifts, chemical modification of the R865 primer was performed (FIG. 2). Oligonucleotides R930, R931, and R932 were dye-labeled with the BODIPY® dyes listed in FIG. 1 and purified by RP-HPLC. As shown in FIG. 3, increasing the linker arm length from $(CH_2)_6$ to $(CH_2)_{12}$ (R932) or addition of one 5' base plus $(CH_2)_3$ (R930) or $(CH_2)_6$ (R931) linker arm lengths slowed the mobility of BODIPY® 503/512-, BODIPY® 530/550-, and BODIPY® 564/570-labeled termination products. In fact, BODIPY® 503/512-R930, labeled termination reactions mimicked the spacing pattern of FAM-R865, BODIPY® 523/547-R931 and BODIPY® 530/550-R930 mimicked the spacing pattern of JOE-R865, BODIPY® 558/568-R930 and BODIPY® 564/570-R930 mimicked the spacing pattern of TAMRA-R865, and BODIPY® 576/589-R931, BODIPY® 581/591-R930, and BODIPY® 589/616-R865 mimicked the spacing pattern of ROX-R865, respectively, (compare highlighted boxes).

EXAMPLE 2

4,4-Difluoro-4-bora-3A,4A-diaza-s-indacene (BODIPY®) Dyes Do Not Require Differential Labeling or Software Correction for Discrepancies in Mobility Additionally and particularly distinctively, the overwhelming majority of BODIPY® fluorophores alter the mobility of termination products in the same way, thus nullifying the need for chemical alteration of the fluorophore or software correction to generate accurate, evenly-spaced DNA sequences. Thus, due to their improved spectral qualities, the use of BODIPY® fluorophores leads to improved DNA sequencing in general and, due to their effect (or lack of differential effect) on electrophoretic mobility, the use of BODIPY® fluorophores leads to improved automated DNA sequencing in particular.

A. Reagents

DNA synthesis reagents were purchased from Applied Biosystems, Inc. (ABI). Oligonucleotides were synthesized trityl-on (0.2 μmole scale) using either an ABI model 380B or model 394 DNA synthesizer and purified using NENSORB™ 20 columns according to the manufacturer's protocol (du Pont de Nemours & Co.). BODIPY® 523/547 propionic acid (PA), and all BODIPY®-succinimidyl ester (SE) dyes were purchased from Molecular Probes. BODIPY®-SE dyes were resuspended in anhydrous DMSO (50 mg/mL), and BODIPY® 523/547-PA was converted to BODIPY® 523/547-SE according to the manufacturer's protocol.

B. Preparation of fluorescent primers

Purified R930 primers (0.4 μmole) was resuspended in 160 μL of 0.5M $NaHCO_3/Na_2CO_3$ (pH 9.0) buffer and divided into four aliquots. To each tube, 5 μL of BODIPY® 503/512-SE, BODIPY® 564/570-SE, or BODIPY® 581/591-SE was added. To the fourth tube, 35 μL of 0.25M $NaHCO_3/Na_2CO_3$, pH 9.0 buffer and 30 μL BODIPY® 523/547-SE were added. Reactions were incubated at 25° C. for 16 h. Following ethanol precipitation, dye-labeled primers were purified by reverse-phase high performance liquid chromatography (RP-HPLC). Fluorescent primers were resuspended in deionized (D.I.) water and diluted to 0.4 pmol/μL.

C. RP-HPLC purification of oligonucleotides

The RP-HPLC hardware system used consists of a Beckman model 127 gradient solvent module, a Rheodyne model 7125 injector, an Applied Biosystems (ABI) model 759A absorbance detector, and a Spectra-Physics model SP4600 DataJet integrator. Gradient RP-HPLC was performed using an ABI aquapore RP-300 column (4.6 mm×250 mm) where "Buffer A" is 100 mM triethylammonium acetate (TEAA), pH 7.0, and "Buffer B" is 100 mM TEAA, 70% (v/v) acetonitrile. Dye-labeled oligonucleotides were purified using the following gradient conditions: 20% Buffer B, 5 min.; 20%–40% Buffer B, 30 min.; 40%–100% Buffer B, 18 min.; 100% Buffer B, 5 min. at a flow rate of 1.0 mL per min.

D. Results

Figure 4A:
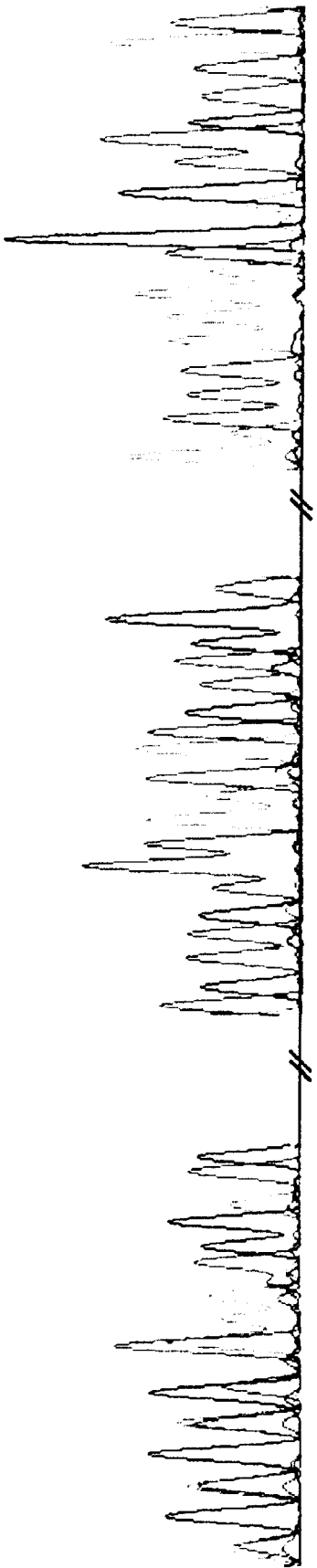
FIGS. 4A through 4C: Demonstrates that BODIPY® dye-labeled primers do not require gel mobility correction. −21M13 primers and BODIPY® primers were used to sequence two different M13 clones by cycle sequencing. 21M13 primers contain FAM-"C", JOE-"A", TAMRA-"G", AND ROX-"T" dye labels and BODIPY® primers contain BODIPY® 503/512-"C", BODIPY® 530/550-"A", BODIPY® 564/570-"G", BODIPY® 581/591-"T" dye labels. Arrows above the sequence chromatograms highlight base calling errors, and the approximate base regions from the primer peak are listed.
Figure 4B:
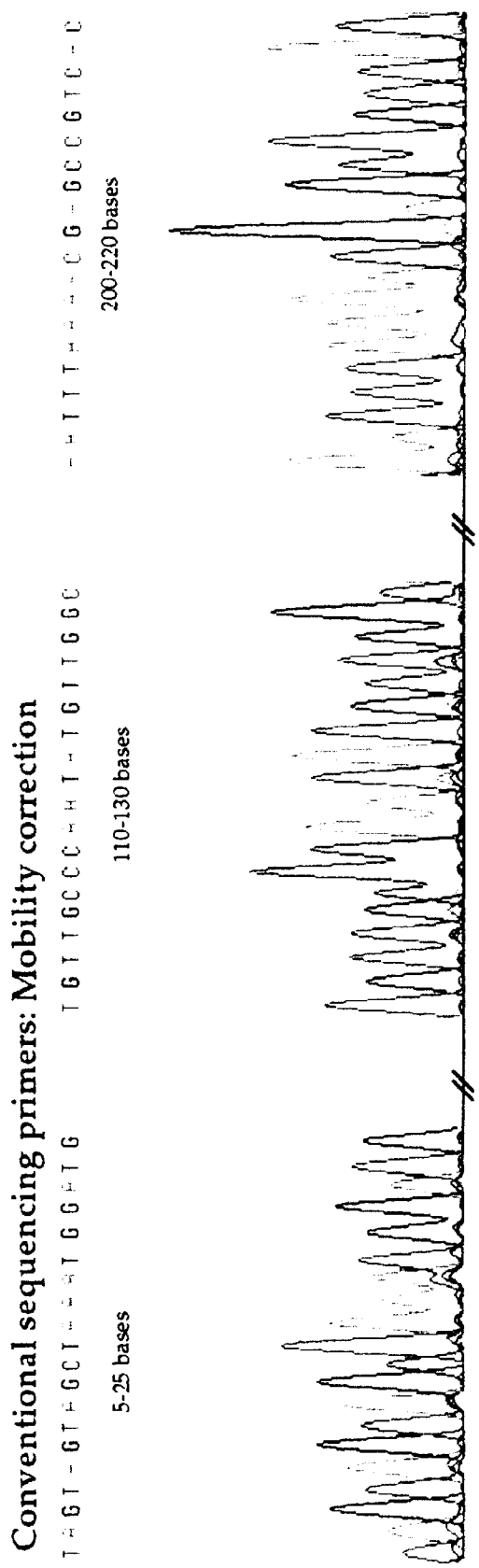
Figure 4C:
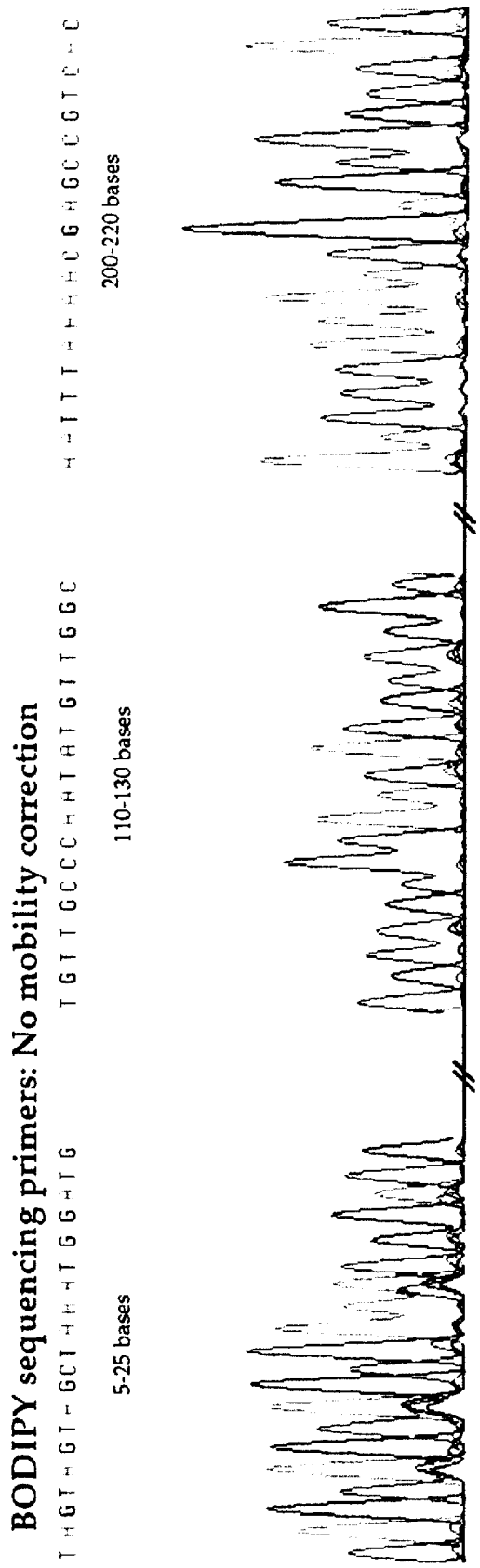
Figure 6B:
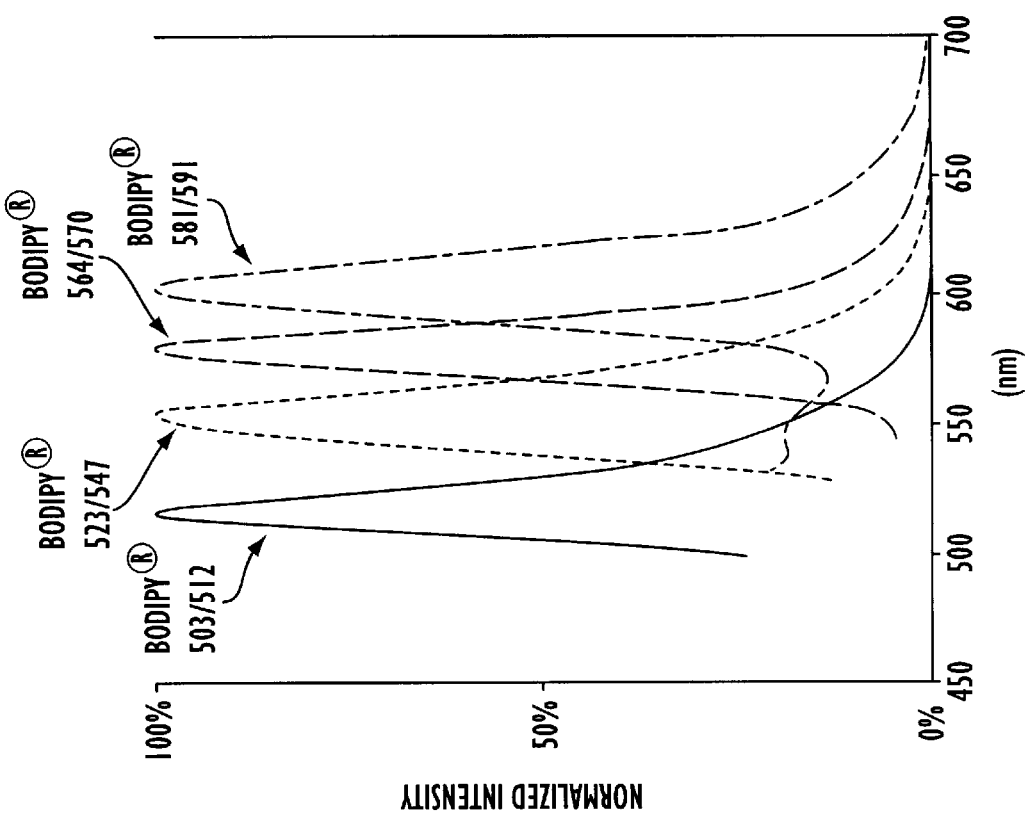
FIGS. 6A and 6B: Depicts normalized emission spectra of four conventional dye-primers and BODIPY® dye-primers.
Figure 6A:
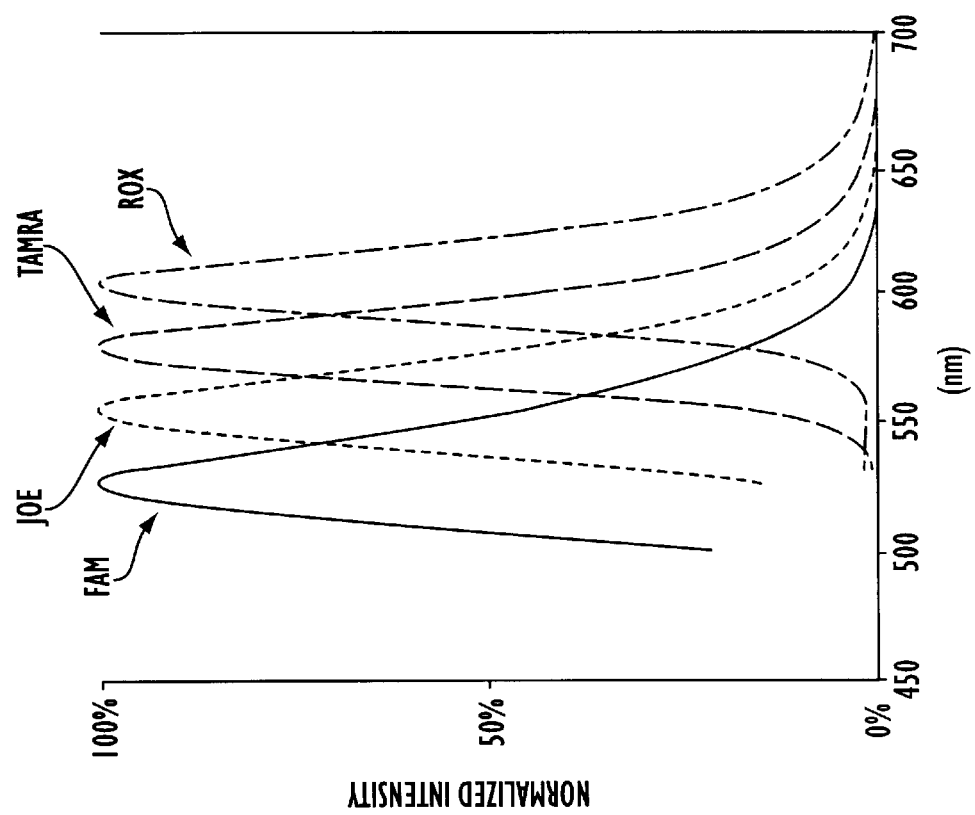

Different BODIPY® dyes do not alter significantly gel mobility. The striking observation that the same linker arm modification was required to substitute BODIPY® dyes for conventional dyes (see Example 1, above) led to the discovery that BODIPY® dyes could generate accurate, evenly-spaced DNA sequencing data without software correction for discrepancies in mobility. BODIPY® 503/512-"C", BODIPY® 530/550-"A", and BODIPY® 564/570-"G", and BODIPY® 581/591-"T" were chosen based on their chemical structure similarity. FIG. 4 shows the comparison of DNA sequencing reads generated from four conventional dye-primers and four BODIPY® dye-primers using two different M13 clones. FIG. 6 depicts the normalized emission spectra of four conventional dye-primers and BODIPY® dye-primers. It is important to note that all BODIPY® dyes were tethered to the primer via the tethers in FIG. 2, and that no differential linker or nucleotide modification was required to achieve a precise, evenly-spaced, easily-read sequence reading.

EXAMPLE 3

Method for 4,4-Difluoro-4-bora-3A,4A-diaza-s-indacene (BODIPY®) Energy Transfer (BET) Primers To increase the emission intensity, doubly-labeled dye-primers were constructed and evaluated for fluoroescence energy transfer (ET). To achieve efficient ET and maximimal signal, oligonucleotides were systematically substituted with the acceptor dye at base increments away from either a FAM donor (0 to 3 bases apart) or a BODIPY® 503-512 donor (1 to 6 bases apart). It was observed that ET efficiency decreased with increasing distance, and decreased with decreasing spectral overlap between donor and acceptor dyes.

A. Reagents

DNA synthesis reagents were purchased from ABI except 5'-amino-modifier C3, C6, and C12, and amino modifier C6 dT phosphoramidites were purchased from Glen Research. Oligonucleotides FET and BET primers were synthesized trityl-on, using either an ABI model 380B or model 394 DNA synthesizer. BODIPY® 523/547 propionic acid (PA), and all BODIPY®-SE dyes were purchased from Molecular Probes. BODIPY®-SE dye were resuspended in anhydrous DMSO (50 mg/mL), and BODIPY® 523/547-PA was converted to BODIPY® 523/547-SE according to the manufacturer's protocol.

B. Fluorescent primers

The donor dye for the FET-3 primer (5'-FAM-T.GTAAAACGACGGCCAGT was synthesized (0.2 μmole)

using 6-FAM amidite and C6dT (T.) and was ethanol precipitated. The donor dye for the BET-3 primer (5'-NTT.GTAAAACGACGGCCAGT, was synthesized (0.2 μmole) using either C3 or C6 amino link (N) and C6dT (T.) and resuspended in 200 μL of 0.1N NaOH. To BET-3 primer, 10 μL of BODIPY® 503/512-SE was added, incubated at 25° C. for 10 min., ethanol precipitated, incubated in 200 μL of 80% acetic acid for 20 min., and ethanol precipitated. Both FET-3 and BET-3 primers were each resuspended in 160 μL of 0.25M NaHCO₃/Na₂CO₃, pH 9.0 buffer and divided into four aliquots. To three tubes, 3 μL of either BODIPY® 503/512-SE, BODIPY® 564/570-SE, or BODIPY® 581/591-SE, respectively was added. To the fourth tube, 35 μL of 0.25M NaHCO₃/Na₂CO₃, pH 9.0 buffer and 30 μL BODIPY® 523/547-SE were added. All dye labeling reactions were incubated at 25° C. for 16 h. Following ethanol precipitation, dye-labeled primers were purified by RP-HPLC, resuspended in 10 mM Tris-HCl, pH 8.0 and 1 mMEDTA, and diluted to 0.4 pmol/μL.

C. RP-HPLC

The RP-HPLC hardware system consisted of a Beckman model 127 gradient solvent module, a Rheodyne model 7125 injector, an Applied Biosystems (ABI) model 759A absorbance detector, and a Spectra-Physics model SP4600 DataJet integrator. Gradient RP-HPLC was performed using an ABI aquapore RP-300 column (4.6 mm×250 mm) where "Buffer A" is 100 mM triethylammonium acetate (TEAA), pH 7.0 and "Buffer B" is 100 mM TEAA, 70 % (v/v) acetonitrile. Dye-labeled oligonucleotides were purified using the following gradient conditions: 20% B, 5 min.; 20% B–40% B, 30 min.; 40% B–100% B, 18 min.; 100% B, 5 min. at a flow rate of 1.0 mL per min.

D. Results

A three base separation between either the FAM donor (FET-3) or the BODIPY® 503–512 donor (BET-3) (FIG. 2B), and acceptor dyes was observed to give the greatest signal enhancement for BODIPY® 564/570 and BODIPY® 581/591 dyes, consistent with FAM-TAMRA and FAM-ROX dye pairs. However, BET-3 dye primers showed considerably greater ET efficiencies and signal enhancements over FET-3 dye primers. See Table 1.

TABLE 1

| Acceptor dyes | Signal enhancements | | ET efficiencies | |
|---|---|---|---|---|
| | BET-3 | FET-3 | BET-3 | FET-3 |
| BODIPY ® 503/512 | 154% | 80% | | |
| BODIPY ® 523/547 | 91% | 35% | 99% | 93% |
| BODIPY ® 564/570 | 360% | 200% | 99% | 92% |
| BODIPY ® 581/591 | 540% | 470% | 98% | 67% |

For BODIPY® 503/512 and BODIPY® 523/547 acceptor dyes, BET-3 dye-primers showed approximately the same signal strength compared to their single dye counterpart, but significant signal loss was observed for the FET-3 dye primers. Comparison of the normalized, overlapping spectral profiles of BET-3 dye-primers was indistinguishable from the single BODIPY® dye-primer spectra shown in FIG. 3, consistent with efficient ET. Overall, the strong signal enhancement of the weaker fluorescent dyes contrasted with minimal enhancements of the normally stronger fluorescent dyes to produce a four dye-primer set with roughly balanced signal intensities.

The sensitivity of the complete BET-3 primer set was examined by serial dilutions of DNA template using an ABI 377A DNA sequencer on a single gel and sufficient signal was correctly analyzed even with a sixteen-fold reduction. This increased sensitivity of BET-3 dye-primers enables the direct loading of sequencing reactions onto gels without a previously-required laborious concentration step.

The unprocessed fluorescent signals generated from BET-3 sequencing reactions demonstrates the benefits of the uniform mobility, properly-balanced signal outputs and improved spectral purity of the present method. The raw data from BET-3 reactions generates a DNA sequencing pattern that is visually interpretable and agrees well with the corresponding analyzed data. In contrast, no discernable sequence pattern could be detected from the unprocessed signals of conventional primers. FIG. 4.

EXAMPLE 4

Method for Phosphoramidite Labeling

A. Reagents

6-Aminohexanol, 2-cyanoethyl N,N-diisopropylchlorophosphoramidite, N,N-diisopropylethylamine, and all solvents were purchased from Aldrich. Amine-VN-phosphoramidite was purchased from CLONTECH. BODIPY®-SE dyes were purchased from Molecular Probes and resuspended in anhydrous DMSO (50 mg/mL). FAM-NHS was purchased from ABI.

B. Synthesis

Figure 5:
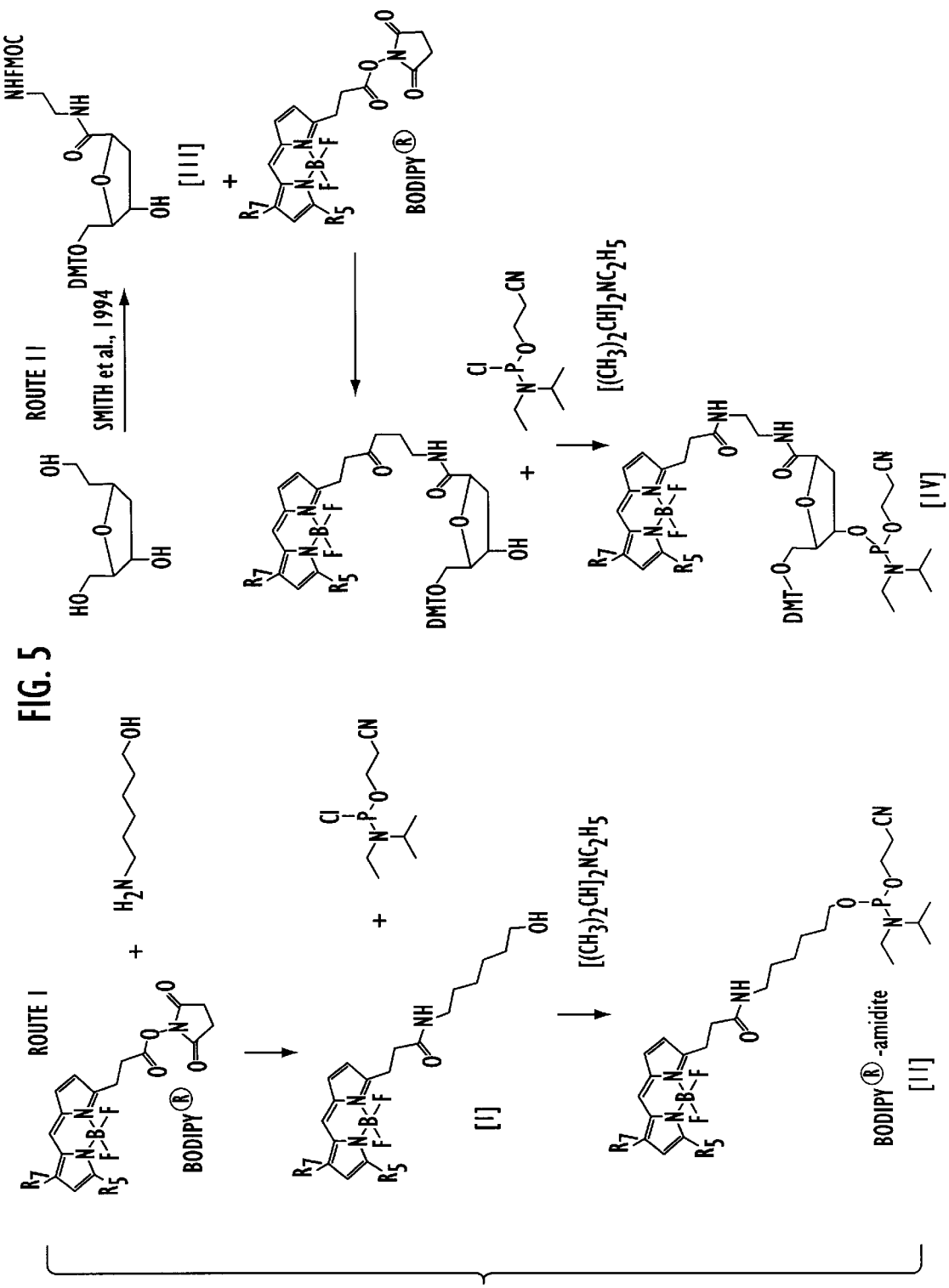
FIG. 5: A general synthetic scheme for end labeling (Route I) and internal labeling (Route II) BODIPY® phosphoramidites is depicted. For specific BODIPY® chemical structures, see FIG. 1.

The general synthesis for two different schemes (route I and II) is outlined in FIG. 5.

Route I: Compound [I]

6-aminohexanol (1 g, 8.5 mmol) is dried by co-evaporation with pyridine (2×10 mL; HPLC grade) under reduced pressure. Residual pyridine is removed by evacuation at 0.1 mm Hg for 2 hours. The solid in methylene chloride (20 mL) is dissolved, and while stirring, freshly distilled diisopropylethylamine (3 mL, 17 mmol) is added. To the solution, a solution of BODIPY®-SE (8.5 mmol) in methylene chloride (10 mL) is added through a dropping funnel under an inert atmosphere. After 30 min of stirring, the progress of the reaction is monitored by thin layer chromatography (TLC). The reaction is usually complete in 1 hour. When the reaction is complete, the reaction mixture is washed with 5% NaHCO₃ solution (3×15 mL), followed by saturated NaCl solution (15 mL). After drying the methylene chloride solution over anhydrous Na₂SO₄, the solvent is evaporated on a rotary evaporator to a yellow oil.

Route I: Compound [II]

Dye-labeled hexanol (6 mmol) is dried under high vacuum for 3 hours and dissolved in freshly distilled THF (from sodium metal and benzophenone, 10 mL). Diisopropylethylamine (1 mL, 6 mmol) is added and the solution is stirred at 0° C. for 10 minutes. 2-cyanoethyl N,N-diisopropylchlorophosphoramidite (1.7 mL, 7.5 mmol) is added dropwise through a syringe under an argon atmosphere. The amine hydrochloride should precipitate within 5 minutes of addition. The mixture should be stirred for 30 minutes at 0° C. and then stirred at room temperature for 1 hour. The progress of the reaction is monitored by TLC. When the reaction is complete, the amine hydrochloride is removed by filtering through a sintered glass funnel under argon and the solid is washed with dry THF (2×10 mL). The combined filtrate is evaporated to a viscous oil on a rotary evaporator. The viscous oil is then dissolved in argon-purged ethyl acetate and the solution is washed with ice-cold 5% aqueous NaHCO₃ solution (2×10 mL) followed by saturated NaCl (10 mL). The ethyl acetate solution is dried over anhydrous NASO₄, filtered, and the filtrate is concentrated to a yellow oil on a rotary evaporator.

Route II: Compounds [III] and [IV]

2'-deoxyribosyl moiety [III] (Smith et al., 1994) is dissolved in piperidine, DMF. To this solution, a solution of BODIPY®-SE (8.5 mmol) in DMF (10 mL) is added under an inert atmosphere. Diisopropylethylamine (1 mL, 6 mmol) is added and the solution is stirred at 0° C. for 10 minutes. 2-cyanoethyl N,N-diisopropylchlorophosphoramidite (1.7 mL, 7.5 mmol) is then added dropwise through a syringe under an argon atmosphere. The amine hydrochloride should precipitate within 5 minutes. This mixture is then stirred for 30 minutes at 0° C. and at room temperature for 1 hour. The progress of the reaction is monitored by TLC. When the reaction is complete, amine hydrochloride is removed by filtering through a sintered glass funnel under argon and the solid is washed with dry THF (2×10 mL). The combined filtrate is evaporated to a viscous oil on a rotary evaporator and the viscous oil is then dissolved in argon-purged ethyl acetate and washed with ice-cold 5% aqueous $NaHCO_3$ solution (2×10 mL), followed by saturated NaCl (10 mL). The ethyl acetate solution is then dried over anhydrous $Na_2SO_4$, filtered, and concentrated to a yellow oil on a evaporate rotary evaporator.

C. Purification

Route I: Compound [I]

A glass column is packed with 100 g silica gel-60 using a mixture of methanol: ethyl acetate: methylene chloride: (0.5:6.0:93.5 v/v/v) containing 1% pyridine. The yellow oil is dissolved in 10 mL of the above solvent mixture and the solution is loaded onto the column. A mixture of methanol ethyl acetate: dichloromethane (1:12:87 v/v/v) is used to elute the column and fractions are collected. Each fraction is checked for absorbance at the absorption wavelength maximum of the BODIPY® dye. Pooled fractions are then evaporated on a rotary evaporator and the residue is dried to constant weight on high vacuum.

Route I: Compound [II]

A glass column is packed with 50 g silica gel-60 using a mixture of methanol: ethyl acetate: methylene chloride: (0.5:6.0:93.5 v/v/v) containing 1% pyridine. The silica column is washed with a one-column volume of 25% ethyl acetate in hexane. The sample is dissolved in a minimum volume of 50% ethyl acetate in hexane and loaded onto the column. The column is then eluted with 25% ethyl acetate in hexane and fractions are collected. The fractions are monitored by TLC (50% ethyl acetate in hexane). The product is detected by shortwave V, and the desired fractions are combined and concentrated under reduced pressure using a rotary evaporator.

Route II: Compounds [III] and [IV]

A glass column is packed with 50 g silica gel-60 using a mixture of methanol: ethyl acetate: methylene chloride: (0.5:6.0:93.5 v/v/v) containing 1% pyridine. The silica column is washed with one column volume of 25% ethyl acetate in hexane. The sample is then dissolved in a minimum volume of 50% ethyl acetate in hexane and loaded onto the column. The column is eluted with 25% ethyl acetate in hexane and fractions are collected. The fractions are monitored by TLC (50% ethyl acetate in hexane). The product is detected by shortwave UV. The desired fractions are collected and concentrated under reduced pressure using a rotary evaporator.

One skilled in the art will appreciate readily that the present invention is well adapted to carry out the objects and obtain the ends and advantages mentioned, as well as those inherent therein. The oligonucleotides, dyes, methods, procedures and techniques described herein are presently representative of the preferred embodiments, are intended to be exemplary, and are not intended as limitations on the scope of the invention. Changes therein and other uses will occur to those skilled in the art, and are encompassed within the spirit of the invention or defined by the scope of the appended claims. All references specifically cited herein are incorporated by reference.

We claim:

1. A method for distinguishing polynucleotides having different 3'-terminal dideoxynucleotides in any method of DNA sequencing requiring electrophoresis of products of the sequencing reactions, the method comprising the steps of:

forming a first, a second, a third, and a fourth class of polynucleotides by extending from primers a plurality of polynucleotides by means of a DNA polymerase or a reverse transcriptase in the presence of dideoxyadenosine triphosphate, dideoxycytosine triphosphate, dideoxyguanosine triphosphate, and dideoxythymidine triphosphate, wherein said first class of polynucleotides has a 3'-terminal dideoxyadenosine and is labeled at a 5' position with a first fluorophore; said second class of polynucleotides has a 3'-terminal dideoxycytidine and is labeled at a 5' position with a second fluorophore; each polynucleotide in the third class said third class of polynucleotides has a 3'-terminal dideoxyguanosine and is labeled at a 5' position with a third fluorophore; and said fourth class of polynucleotides has a 3'-terminal dideoxythymidine and is labeled at a 5' position with a fourth fluorophore; wherein at least one of said fluorophores is a 4,4-difluoro-4-bora-3A,4A-diaza-s-indacene (BODIPY®) fluorophore, wherein at least one other fluorophore is used, and, wherein if said first, second, third and fourth fluorophores are all different, said polynucleotides can be electrophoresed in a same or a different lane, and wherein if any of said first, second, third or fourth fluorophores are the same, said polynucleotides labeled with said same fluorophores are electrophoresed in separate lanes;

electrophoretically separating on a gel by size the polynucleotides;

illuminating with an illumination beam the bands on the gel, the illumination beam having a wavelength capable of causing the fluorophores to fluoresce; and identifying the classes of polynucleotides in the bands by the fluorescence or absorption spectrum of the fluorophores.

2. A method for distinguishing polynucleotides having different 3'-terminal dideoxynucleotides in a chain termination method of DNA sequencing, the method comprising the steps of:

forming a first, a second, a third, and a fourth class of polynucleotides by extending from primers a plurality of polynucleotides by means of a DNA polymerase or a reverse transcriptase in the presence of dideoxyadenosine triphosphate, dideoxycytosine triphosphate, dideoxyguanosine triphosphate, and dideoxythymidine triphosphate, wherein said first class of polynucleotides has a 3'-terminal dideoxyadenosine and is labeled at a 5' position with BODIPY® 523/547, BODIPY® 530/550 or 2',7'-dimethoxy-4', 5'-dichloro-6-carboxyfluorescein (JOE); said second class of polynucleotides has a 3'-terminal dideoxycytidine and is labeled at a 5' position with BODIPY® 503/512 or 5-carboxyfluorescein (FAM); said third class of polynucleotides has a 3'-terminal dideoxyguanosine and is labeled at a 5' position with BODIPY® 558/568, BODIPY® 564/

570 or N,N,N',N'-tetramethyl-6-carboxy-rhodamine (TAMRA); and said fourth class of polynucleotides has a 3'-terminal dideoxythymidine and is labeled at a 5' position with BODIPY® 576/589, BODIPY® 581/591, BODIPY® 589/616, or 6-carboxy-X-rhodamine (ROX); wherein at least one of said classes is labeled with a BODIPY® fluorophore;

electrophoretically separating on a gel by size the polynucleotides;

illuminating with an illumination beam bands on the gel, the illumination beam having a wavelength capable of causing the fluorophores to fluoresce; and identifying the classes of polynucleotides in the bands by the fluorescence or absorption spectrum of the fluorophores.

3. A method for distinguishing polynucleotides having different 3'-terminal dideoxynucleotides in a chain termination method of DNA sequencing, the method comprising the steps of:

forming a first, a second, a third, and a fourth class of polynucleotides by extending from primers a plurality of polynucleotides by means of a DNA polymerase or a reverse transcriptase in the presence of dideoxyadenosine triphosphate, dideoxycytosine triphosphate, dideoxyguanosine triphosphate, and dideoxythymidine triphosphate, wherein said first class of polynucleotides has a 3'-terminal dideoxyadenosine and is labeled at a 5' position with a first BODIPY® fluorophore; second class of polynucleotides has a 3'-terminal dideoxycytidine and is labeled at a 5' position with a second BODIPY® fluorophore; said third class of polynucleotides has a 3'-terminal dideoxyguanosine and is labeled at a 5' position with a third BODIPY® fluorophore; and fourth class of polynucleotides has a 3'-terminal dideoxythymidine and is labeled at a 5' position with a fourth BODIPY® fluorophore; wherein said first, second, third and fourth BODIPY® fluorophores are all different;

electrophoretically separating on a gel by size the polynucleotides;

illuminating with an illumination beam bands of said gel, said illumination beam having a wavelength capable of causing said BODIPY® fluorophores to fluoresce; and identifying the classes of polynucleotides in the bands by the fluorescence or absorption spectrum of the dyes.

4. The method of claims 1, 2, or 3, wherein said BODIPY® fluorophores have an adsorption maxima of about 450 to 700, and an emission maxima of about 450 to 700.

5. The method of claims 1, 2, or 3, wherein said BODIPY® fluorophores have adsorption maxima of about 480 to 650, and an emission maxima of about 480 to 650.

6. The method of claims 2 or 3, wherein said chain termination method of DNA sequencing is performed by an automated DNA sequencing instrument.

7. The method of claims 1, 2, or 3, wherein said DNA polymerase is selected from the group of Thermosequenase, Klenow fragment, SEQUENASE® DNA polymerase, Bst DNA polymerase, AMPLITAQ® DNA polymerase, Pfu (exo-)DNA polymerase, rTth DNA polymerase or Vent (exo-) DNA polymerase, and the reverse transcriptase is selected from the group of AMV-RT or M-MuLV-RT.

8. The method of claim 1, 2, or 3, wherein said BODIPY® fluorophores are coupled to a primer suitable for sequencing by a linker.

9. The method of claim 8, wherein said linker has the formula $(CH_2)_n$, where n=1–30.

10. The method of claim 9, wherein said linkers are selected from the group of $(CH_2)_3$, $(CH_2)_6$, and $(CH_2)_{12}$.

11. The method of claim 1, 2, or 3, wherein said BODIPY® fluorophore is attached at the 5' end of the products of the sequencing reaction and an additional fluorophore is attached at a 3' position of the product of the sequencing reaction or at one or more internal positions of the products of the sequencing reaction.

12. The method of claim 11, wherein said additional fluorophore is a BODIPY® fluorophore.

13. The method of claim 11, wherein said additional fluorophore is FAM.

14. The method of claim 14, wherein said additional fluorophore has an adsorption maxima of about 475 to 650.

15. The method of claim 14 wherein said additional fluorophore is BODIPY® 523/547.

16. The method of claim 14, wherein said additional fluorophore is BODIPY® 503/512.

17. A method for distinguishing polynucleotides having different 3'-terminal dideoxynucleotides in the chain termination method of DNA sequencing, the method comprising the steps of:

forming a first, a second, a third, and a fourth class of polynucleotides by extending from primers a plurality of polynucleotides by means of a DNA polymerase or a reverse transcriptase in the presence of dideoxyadenosine triphosphate, dideoxycytosine triphosphate, dideoxyguanosine triphosphate, and dideoxythymidine triphosphate, wherein each polynucleotide in the first class has a 3'-terminal dideoxyadenosine and is labeled at a 5' position with BODIPY® 523/547 or BODIPY® 530/550; each polynucleotide in the second class has a 3'-terminal dideoxycytidine and is labeled at a 5' position with BODIPY® 503/512; each polynucleotide in the third class has a 3'-terminal dideoxyguanosine and is labeled at a 5' position with BODIPY® 564/570; and each polynucleotide in the fourth class has a 3'-terminal dideoxythymidine and is labeled at a 5' position with BODIPY® 581/591 or BODIPY® 576/589;

electrophoretically separating on a gel by size the polynucleotides;

illuminating with an illumination beam bands on the gel, the illumination beam having a wavelength capable of causing the fluorophores to fluoresce; and identifying the classes of polynucleotides in the bands by the fluorescence or absorption spectrum of the fluorophores.

18. A method for distinguishing polynucleotides having different 3'-terminal dideoxynucleotides in the chain termination method of DNA sequencing, the method comprising the steps of:

forming a first, a second, a third, and a fourth class of polynucleotides by extending from primers a plurality of polynucleotides by means of a DNA polymerase or a reverse transcriptase in the presence of dideoxyadenosine triphosphate, dideoxycytosine triphosphate, dideoxyguanosine triphosphate, and dideoxythymidine triphosphate, wherein each polynucleotide in the first class has a 3'-terminal dideoxyadenosine and is labeled at a 5' position with BODIPY® 523/547 or BODIPY® 530/550; each polynucleotide in the second class has a 3'-terminal dideoxycytidine and is labeled at a 5' position with BODIPY® 581/591 or BODIPY® 576/589; each polynucleotide in the third class has a 3'-terminal dideoxyguanosine and is labeled at a 5' position with BODIPY® 503/512; and each polynucleotide in the fourth class has a 3'-terminal dideoxythymidine and is labeled at a 5' position with BODIPY® 564/570;

electrophoretically separating on a gel by size the polynucleotides;

illuminating with an illumination beam bands on the gel, the illumination beam having a wavelength capable of causing the fluorophores to fluoresce; and identifying the classes of polynucleotides in the bands by the fluorescence or absorption spectrum of the fluorophores.

19. A substituted 4,4-difluoro-4-bora-3A,4A-diaza-s-indacene (BODIPY®) compound as an amidite.

* * * * *